(12) United States Patent
Wosikowski-Buters et al.

(10) Patent No.: US 8,048,888 B2
(45) Date of Patent: Nov. 1, 2011

(54) ANTI-PROLIFERATIVE COMBINATION THERAPY USING CERTAIN PLATINUM-BASED CHEMOTHERAPEUTIC AGENTS AND EGFR INHIBITORS OR PYRIMIDINE ANALOGUES

(75) Inventors: Katja Wosikowski-Buters, Poing (DE); Christoph Schaab, München (DE); Marino Schuhmacher, München (DE); Franz Obermayr, Moorenweis/Grunertshofen (DE); Igor Ivanov, Markt Indersdorf (DE)

(73) Assignee: Agennix AG, Heidelberg (DE)

( * ) Notice: Subject to any disclaimer, the term of this patent is extended or adjusted under 35 U.S.C. 154(b) by 395 days.

(21) Appl. No.: 12/084,740

(22) PCT Filed: Nov. 13, 2006

(86) PCT No.: PCT/EP2006/068381
§ 371 (c)(1),
(2), (4) Date: May 9, 2008

(87) PCT Pub. No.: WO2007/054573
PCT Pub. Date: May 18, 2007

(65) Prior Publication Data
US 2009/0175856 A1 Jul. 9, 2009

(30) Foreign Application Priority Data
Nov. 11, 2005 (EP) .................................... 05024701

(51) Int. Cl.
*A01N 43/54* (2006.01)
(52) U.S. Cl. ..................................... 514/266.4; 514/274
(58) Field of Classification Search .................... 514/183
See application file for complete search history.

(56) References Cited

U.S. PATENT DOCUMENTS

2006/0019268 A1* 1/2006 Cheng et al. ..................... 435/6
2006/0069101 A1* 3/2006 Kim et al. ................ 514/252.19

FOREIGN PATENT DOCUMENTS

WO WO 2004/096224 11/2004
WO WO 2005/095651 10/2005

OTHER PUBLICATIONS

Kelland L.R. (Overcoming Resistance to Platinum Therapy in Patients with Advanced Cancer, Am J Cancer 2002: 1 (4): 247-255).*

Belliere et al., *Oncologie*, 4(6): 368-372 (2002) (not enclosed herewith).
Cunningham et al., *Cancer Treatment Reviews*, 27(4): 211-220 (2001).
Demario et al., *Journal of Clinical Oncology*, 16(7): 2562 (1998).
*Deutsche Apotheker Zeitung*, 143(39): 35-36 (2003).
Faivre et al., *Bulletin Du Cancer*, 86(10): 861-865 (1999).
Hinerman et al., *Therapy, Future Drugs*, 1(1): 67-74 (2004) (Abstract only).
Kelland, L.R., *American Journal of Cancer*, 1(4): 247-255 (2002).
Kweekel et al., *Cancer Treatment Reviews*, 31(2): 90-105 (2005).
Pešek et al., *Studia Pneumologica Et Phthiseologica*, 59(1): 14-18 (1999).
Smith, D.C., *Urologic Clinics of North America*, 26(2): 323-331 (1999).
Stokes et al., *Gynecologic Oncology*, 97(3): 790-795 (2005).
Zelek et al., *Journal of Clinical Oncology*, 20(10): 2551-2552 (2002).
Calabresi et al., Section IX Chemotherapy of Neoplastic Diseases—Introduction, Goodman & Gilman's The Pharmacological Basis of Therapeutics 10th ed., (J. Hardman, L. Limbird, and A. Gilman eds.), (McGraw-Hill, New York, 2001) (pp. 1381, 1383-1385 and 1388 provided).
Fokkema et al., "JM216-, JM118-, and cisplatin-induced cytotoxicity in relation to platinum-DNA adduct formation, glutathione levels and p53 status in human tumour cell lines with different sensitivities to cisplatin", *Biochemical Pharmacology*, 63: 1989-1996 (2002).
Gura, T., "Systems for Identifying New Drugs Are Often Faulty", *Science*, 278(5340): 1041-1042 (1997).
Kelland, L.R., "An update on satraplatin: the first orally available platinum anticancer drug", *Exp. Opin. Invest. Drugs*, 9 (6): 1373-1382 (2000).
Petrylak, D.P., "Docetaxel for the Treatment of Hormone-Refractory Prostate Cancer", *Reviews in Urology*, 5(Suppl. 2): S14-S21 (2003).
Vogelstein et al., Chapter 1, in the Genetic Basis of Human Cancer 2nd ed., (B. Vogelstein and K. Kinzler eds.), (McGraw-Hill, 2002) p. 3.

* cited by examiner

*Primary Examiner* — Sreeni Padmanabhan
*Assistant Examiner* — Timothy E Betton
(74) *Attorney, Agent, or Firm* — Leon R. Yankwich; David G. O'Brien; Yankwich & Associates, P.C.

(57) ABSTRACT

The present invention describes a method or uses of prevention and/or treatment of a cancer or a tumor, and in particular to a combination therapy, methods, compositions and pharmaceutical packages comprising an inhibitor of receptors of the EGFR family or a chemotherapeutically active pyrimidine analogue and certain platinum-based chemotherapeutic agents.

20 Claims, 3 Drawing Sheets

Figure 1. Satraplatin (JM216) and its metabolites.
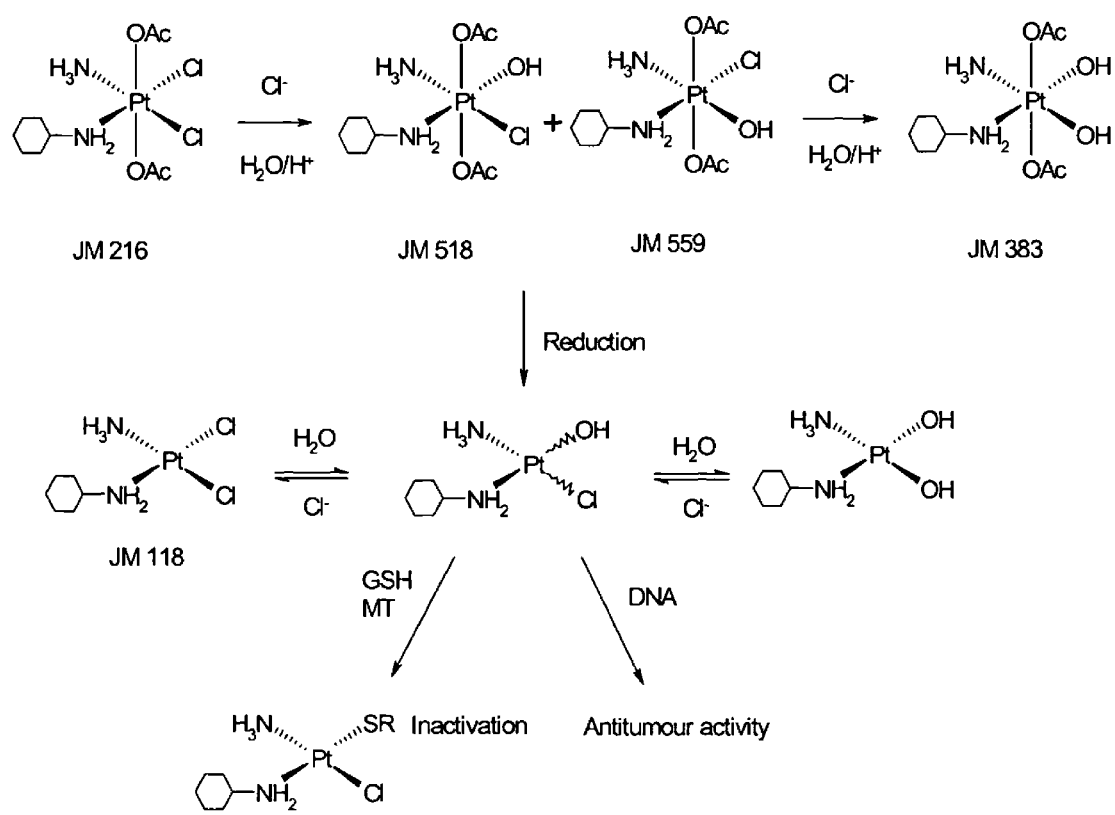

Figure 2. Isobologram, showing that herceptin and JM-118 act synergistically when administered simultaneously
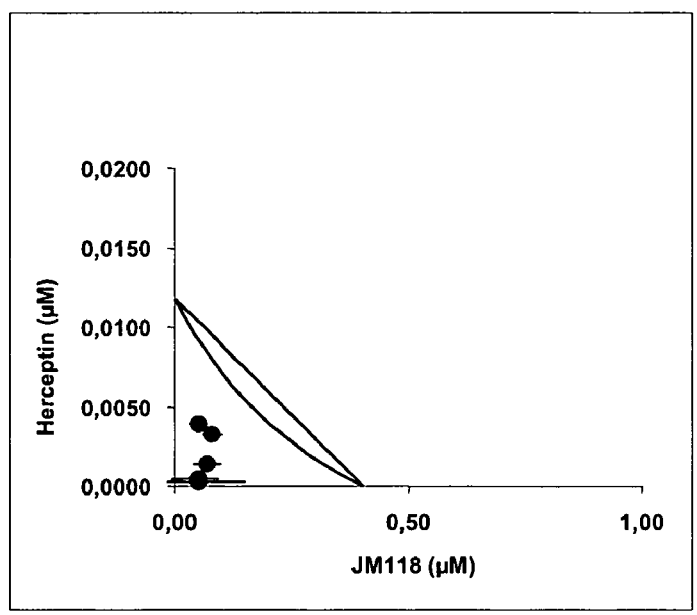

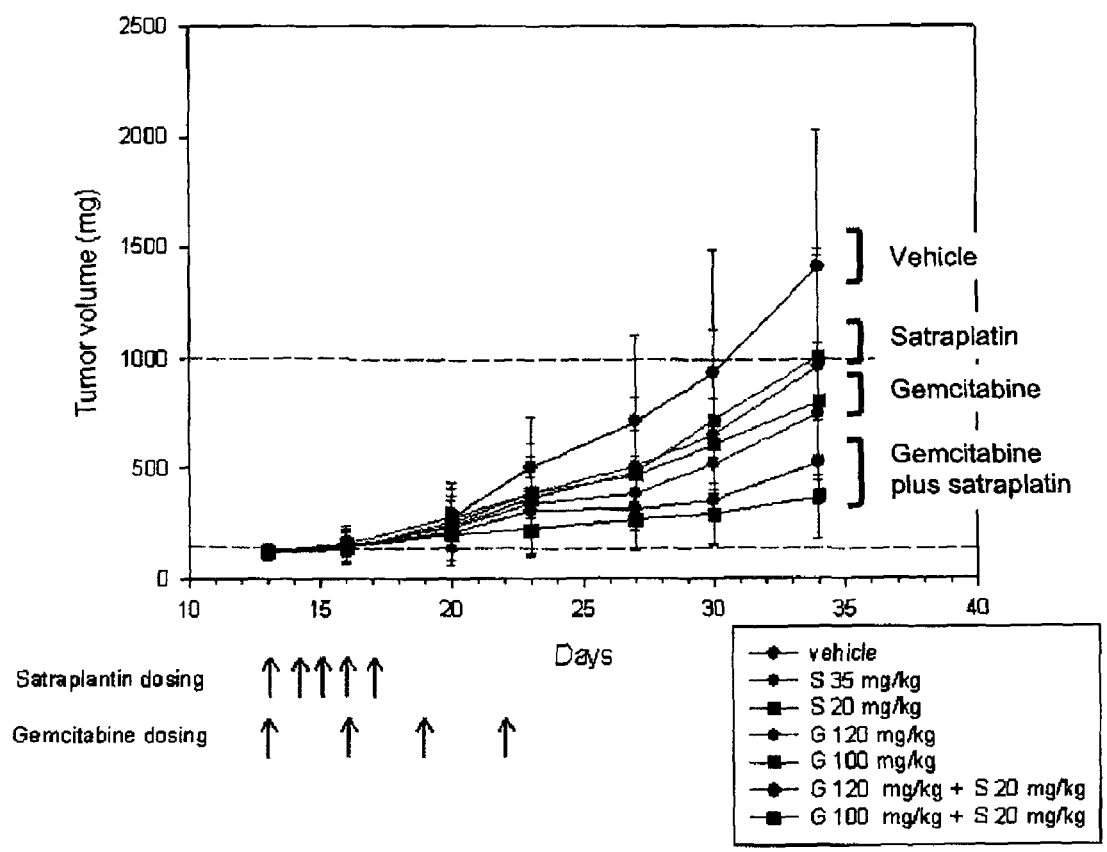
Figure 3. Xenograft model of a combination treatment of satraplatin with gemcitabine in athymic nu/nu mice.

ANTI-PROLIFERATIVE COMBINATION THERAPY USING CERTAIN PLATINUM-BASED CHEMOTHERAPEUTIC AGENTS AND EGFR INHIBITORS OR PYRIMIDINE ANALOGUES

This invention relates to a method or uses of prevention and/or treatment of a cancer or a tumor, and in particular to a combination therapy, methods, compositions and pharmaceutical packages comprising an inhibitor of receptors of the EGFR family or a chemotherapeutically active pyrimidine analogue and certain platinum-based chemotherapeutic agents.

BACKGROUND OF THE INVENTION

Platinum compounds are among the most active chemotherapeutic agents available for the treatment of a variety of cancers and tumors. The use of some of these compounds, e.g., cisplatin, is restricted by both toxological and resistance considerations. To overcome these issues, efforts were started to discover novel platinum compounds which do not share certain properties of cisplatin. One compound that was identified is satraplatin (JM216), a platinum (Pt) IV complex. Satraplatin (JM216) was selected for clinical development because of several advantageous properties: (a) high cytotoxic activity in vitro against several solid tumor cell lines, including cisplatin-resistant ones; (b) in vivo antitumor activity against a variety of murine- and human-xenograft tumor models; (c) a relatively mild toxicity profile (such as the absence of kidney toxicity and neurotoxicity), and (d) oral availability.

In Phase 2 clinical trials, satraplatin showed activity against several different cancers, including prostate, ovarian, and small cell lung (SCL) cancers. In a Phase II-III clinical trial in Hormone Refractory Prostate Carcinoma (HRPC) patients, the combination of satraplatin plus prednisone was more active than prednisone alone (ASCO meeting, 2003; Sternberg et al., Oncology (2005) 68, 2). Satraplatin is currently undergoing Phase 3 development in a worldwide registration clinical study evaluating satraplatin plus prednisone versus placebo plus prednisone as second-line cytotoxic chemotherapeutic treatment against hormone refractory prostate cancer. Recently it was reported that the study data show that the results for progression-free survival (PFS) are highly statistically significant ($p<0.00001$) using the protocol-specified log-rank test. Patients who received satraplatin plus prednisone had a 40% reduction in the risk of disease progression (hazard ratio of 0.6; 95% Confidence Interval: 0.5-0.7) compared with patients who received prednisone plus placebo. The improvement seen in progression-free survival by patients treated with satraplatin increased over time. Progression-free survival at the median (50th percentile) demonstrated a 13% improvement in patients who received satraplatin plus prednisone (11 weeks) compared to patients who received prednisone plus placebo (9.7 weeks). Progression-free survival at the 75th percentile showed an 89% improvement for patients in the satraplatin arm (36 weeks) versus patients in the placebo arm (19 weeks). At 6 months, 30% of patients in the satraplatin arm had not progressed, compared to 17% of patients in the control arm. At 12 months, 16% of patients who received satraplatin had not progressed, compared to 7% of patients in the control arm. All of these analyses were conducted on an intent-to-treat basis. The current standard treatment of HRPC is primarily palliative and includes first line chemotherapeutic regimens with agents such as estramustine, mitoxantrone and taxanes, with docetaxel being increasingly used as a first-line chemotherapeutic agent.

Satraplatin is considerably different from other platinum agents, like e.g. cisplatin. Using a panel of ovarian cancer carcinoma cell lines Kelland et al. (Cancer Res (1992), 52, 822) demonstrated that satraplatin is significantly more cytotoxic than cisplatin, and that satraplatin exhibits selective cytotoxic effects against intrinsically cisplatin-resistant cell lines. Loh et al. (Br. J. Cancer (1992) 66, 1109) confirmed these findings. Loh et al. furthermore came to the conclusion that the increased accumulation of satraplatin, which is a result of its enhanced lipophilicity, accounts for the dramatic increase of the potency of satraplatin over cisplatin. Other studies reporting on the activity of satraplatin towards cell lines with acquired or intrinsic resistance to cisplatin are those of Mellish et al. (Br J Cancer (1993) 68, 240), using human cervical squamous cell carcinoma cell lines, and Orr et al. (Br J Cancer (1994) 70, 415), using murine leukaemia cell lines. In the latter report the cell lines used were not just resistant to cisplatin, but also to tetraplatin and carboplatin.

Furthermore, cisplatin was repeatedly shown not to be effective against prostate cancer. Qazi & Khandekar (Am J Clin Oncol (1983) 6, 203) demonstrated in a phase II trial that cisplatin is not effective in patients with metastatic prostatic carcinoma. Hasegawa et al. (Cancer & Chemother (1987) 14, 3279) reported that the range of effective dose was wider for other platinum agents like carboplatin than for cisplatin. Even in combination treatment, cisplatin-comprising regimens demonstrate limited activity, e.g. in combination with mitoxantrone in metastatic prostate cancer (Osborne et al., Eur J Cancer (1992) 28, 477). Therefore, cisplatin is not a substitute for satraplatin as an agent to be used in prostate cancer.

Twentyman et al. (Cancer Res (1992) 52, 5674) investigated the sensitivity of human lung cancer cell lines with acquired or inherent resistance to cisplatin, to a series of novel platinum compounds, including satraplatin. In this study, cisplatin and carboplatin were found to act very similar, whereas satraplatin did not.

In spite of different routes of administration Kelland et al. (Int J Oncol (1993) 2, 1043) demonstrated the surprising finding that the efficacy of orally administered satraplatin is comparable to that of cisplatin and carboplatin administered intravenously, as determined in human ovarian carcinoma xenograft models. These findings were confirmed by Rose et al. (Cancer Chemother Pharmacol (1993) 32, 197), using murine and human tumor models. McKeage et al. (Cancer Res (1994) 54, 4118) investigated the differences of the schedule dependencies associated with these routes of administration.

In another study by Kelland et al. (Cancer Res (1993) 53, 2581) many of the above mentioned differences between satraplatin and cisplatin were confirmed. Furthermore it was found, that the cytotoxicity of satraplatin was dependent on the time of drug exposure. Again, it was confirmed that satraplatin does not exhibit cross resistance to cisplatin, whereas other platinum agents, e.g. tetraplatin, do. Without being bound to any particular theory, satraplatin circumvents transport-determined acquired resistance to cisplatin.

Mellish et al. (Cancer Res (1994) 54, 6194) investigated the mechanisms of acquired resistance to satraplatin in two human ovarian carcinoma cell lines. They found that, in contrast to cisplatin, acquired resistance to satraplatin is not mediated through reduced drug accumulation, but by increased intracellular GSH levels or increased DNA repair.

Sharp et al. (Clin Cancer Res (1995) 1, 981) compared the transport of cisplatin and satraplatin in human ovarian carcinoma cell lines. Cisplatin transport in the parental cell lines occurs via passive diffusion and active/facilitated transport, whereas in a cisplatin-resistant cell lines cisplatin enters cells by passive diffusion only. Without being bound to any particular theory, satraplatin circumvents cisplatin resistance by increasing the drug uptake. The mechanism of satraplatin transport across cell membranes is through passive diffusion, predominantly as a result of its enhanced lipophilicity.

Fink et al. (Cancer Res (1996) 56, 4881) investigated the effect of the loss of DNA mismatch repair activity on the sensitivity to cisplatin, satraplatin and other platinum agents. In contrast to cisplatin and carboplatin, which form the same type of adducts in DNA, there was no difference in sensitivity between mismatch repair-proficient and mismatch repair-deficient cell lines for satraplatin.

Perego et al. (Mol Pharmacol (1998) 54, 213) investigated the sensitivity of strains of *Schizosaccharomyces pombe* to cisplatin, satraplatin and other platinum compounds. The panel of the 23 yeast strains tested comprised many mutants in genes that affect the response to radiation. Whereas the mutants fell into three groups with respect to their sensitivity to cisplatin (minimal change in sensitivity, hypersensitivity, and marked hypersensitivity), none of the mutants demonstrated an appreciable change in sensitivity to satraplatin.

Leyland-Jones et al. (Amer J. Pathol (1999), 155, 77) investigated genomic imbalances associated with acquired resistance to platinum analogues. Using three ovarian carcinoma cell lines they identified differences between the three platinum compounds cisplatin, satraplatin and AMD473 (picoplatin).

Amorino et al. (Int J Radiation Oncol Biol Phys (1999), 44, 399) investigated radiopotentiation by satraplatin and the role of repair inhibition. They found that satraplatin can potentiate the effects of radiation in human lung cancer cells, and that the mechanism of this effect is probably inhibition of DNA repair by satraplatin. Differences to other platinum drugs like cisplatin and carboplatin are indicated.

Vaisman et al. (Biochemistry (1999), 38, 11026) reported on the effects of DNA polymerases and high mobility group protein 1 on the carrier ligand specificity for translesion synthesis past platinum-DNA adducts, with respect to different platinum compounds.

Screnci et al. (Br J Cancer (2000) 82, 966) investigated the relationship between hydrophobicity, reactivity, accumulation and peripheral nerve toxicity of a series of platinum compounds. According to Screnci et al. the hydrophilicity of platinum drugs correlates with platinum sequestration in the peripheral nervous system, but not with neurotoxicity.

Wei et al. (J Biol Chem (2001) 276, 38774) reported on the effect of ligands on the specific recognition of intrastrand platinum-DNA cross-links by high mobility group box and TATA-binding proteins, with respect to different platinum compounds.

Fokkema et al. (Biochem Pharmacol (2002) 63, 1989) analysed in detail the satraplatin-, JM118-, and cisplatin-induced cytotoxicities in relation to various parameters like platinum-DNA adduct formation, glutathione levels and p53 status in human tumor cell lines with different sensitivities to cisplatin. It was confirmed that satraplatin and JM118 can partially circumvent intrinsic and acquired resistance to cisplatin. At equimolar basis, satraplatin induced lower levels of platinum-DNA adducts in the cell lines tested compared to cisplatin.

Taken together, fundamental differences exist between satraplatin and other platinum agents, such as cisplatin. These differences are the basis, lead to or play a role in many of the different characteristics of satraplatin, including different pharmacokinetic properties, different efficacy, a different toxicology profile, different ADME properties and different mechanisms that lead to drug resistance, only to name a few.

Receptors of the EGFR family are known targets for cancer. We show, as outlined herein, that inhibitors of receptors of the EGFR family act synergistically with certain platinum-based compounds. This synergistic effect is observed with different receptors of the EGFR family, and the synergistic effect is also not limited by the nature of the compound inhibiting the EGFR receptor. We show that antibodies, as well as small molecules, act synergistically with certain platinum-based compounds on cancer cells and tumor cells.

Pyrimidine analogues inhibit the biosynthesis of pyrimidine nucleotides and/or mimic certain metabolites of this pathway. We demonstrate that such compounds act synergistically with certain platinum-based compounds. It is asserted that this synergism is also observed between prodrugs of pyrimidine analogues or compounds that are metabolised to pyrimidine analogues in the human body.

Synergism between inhibitors of receptors of the EGFR family or chemotherapeutically active pyrimidine analogues with platinum-based chemotherapeutic agents have been demonstrated to some extent in the past. Nagourney et al (Oncology (2001) 15, 28) reported synergism between cisplatin and herceptin in breast cancer. Synergism between inhibitors of receptors of the EGFR family and cisplatin was also reported by Gieseg et al. (Anti-cancer drugs (2001) 12, 683). Mosconi et al (Eur J Cancer (1997) reported synergistic effects between gemcitabin and cisplatin.

However, as evidenced above and shown herein there are fundamental differences between the platinum-compounds of the present invention, such as satraplatin and JM-118, and other platinum compound, such as cisplatin, carboplatin and oxaliplatin. No synergistic effects have so far been reported between the platinum-compounds of the present invention and inhibitors of receptors of the EGFR family or chemotherapeutically active pyrimidine analogues.

SUMMARY OF THE INVENTION

This present invention relates to a method of prevention and/or treatment of a cancer or a tumor, and in particular to a combination therapy, methods, compositions and pharmaceutical packages comprising an inhibitor of receptors of the EGFR family or a chemotherapeutically active pyrimidine analogue and certain platinum-based chemotherapeutic agents.

It is an object of the invention to provide a method of killing or inhibiting the growth of a tumor cell comprising contacting said cell with an effective amount of a combination of active ingredients.

Another object of the invention is to provide a method for treating an individual suffering from a tumor or a cancer, comprising administering to the individual an effective amount of said combination of active ingredients.

Yet another object of the invention is the use of one of the active ingredients in the manufacture of a pharmaceutical for use, in combination with the other active ingredient, in the treatment of a cancer or a tumor.

Yet another object of the invention is to provide a therapeutic combination for the treatment or prevention of a cancer or a tumor.

Yet another object of the invention is to provide a pharmaceutical composition for the treatment or prevention of a cancer or a tumor.

Yet another object of the invention is to provide a packaged pharmaceutical comprising a pharmaceutical composition and instructions to administer an effective amount of one pharmaceutical composition to an individual suffering from a cancer or a tumor, prior to the administration of another, second pharmaceutical composition.

It is another object of the invention to provide kits having a combination of active ingredients, with or without pharmaceutically acceptable diluents and carriers, which may be effectively utilized together for carrying out the novel combination therapies of the invention.

The solution offered is based on the surprising discovery that inhibitors of receptors of the EGFR family and chemotherapeutically active pyrimidine analogues are highly synergistic in combination with a platinum-based chemotherapeutic agent selected from:
(a) an orally available platinum-based chemotherapeutic agent;
(b) a platinum-based chemotherapeutic agent comprising a platinum (IV) co-ordination complex;
(c) a platinum-based chemotherapeutic agent represented by the following general structure:

(formula I)

wherein $R_1$ and $R_2$ may be present or absent, each of $R_1$-$R_4$ is independently selected from halogen, hydroxyl, and acetate, and $R_5$ is a cycloalkyl;
(d) satraplatin or a metabolite of satraplatin;
or a pharmaceutically acceptable salt, isomer or prodrug of (a) to (d). This synergistic effect is most pronounced, if the inhibitor of a receptor of the EGFR family or the chemotherapeutically active pyrimidine analogue precedes the platinum-based chemotherapeutic agent.

BRIEF DESCRIPTION OF THE DRAWINGS

FIG. 1. Satraplatin (JM216) and certain of its metabolites according to Raynaud et al. (Cancer Chemother Phamacol (1996), 38, 155-162).

FIG. 2. Isobologram, showing that herceptin and JM-118 act synergistically when administered simultaneously.

FIG. 3. Xenograft model of a combination treatment of satraplatin with gemcitabine in athymic nu/nu mice.

DETAILED DESCRIPTION OF THE INVENTION

1. Definitions

The terms "administered", "administration", "administration of", "administering" a compound will be understood to mean providing any compound of the methods of the invention to an individual in need of treatment.

The term "alkyl" refers to optionally substituted straight- or branched-chain saturated hydrocarbon groups having from 1 to about 20 carbon atoms, preferably from 1 to about 7 carbon atoms. Examples of alkyl include, but are not limited to, methyl, ethyl, n-propyl, i-propyl, n-butyl, s-butyl, t-butyl, n-pentyl, and s-pentyl. In addition, the term is intended to include both unsubstituted and substituted alkyl groups, the latter referring to alkyl moieties having one or more hydrogen substituents replaced by, but not limited to halogen, hydroxyl, carbonyl, alkoxy, ester, ether, cyano, phosphoryl, amino, imino, amido, sulfhydryl, alkylhio, thioester, sulfonyl, nitro, heterocyclo, aryl or heteroaryl. It will also be understood by those skilled in the art that the substituted moieties themselves can be substituted as well when appropriate.

The term "cycloalkyl" refers to optionally substituted saturated monocyclic or polycyclic hydrocarbon ring systems, preferably containing 3 to 7 carbons per ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more of the groups described above as substituents for alkyl groups.

The term "effective amount" means the amount of the inhibitor of a receptors of the EGFR family, of a chemotherapeutically active pyrimidine analogues or the subject compound, or the EGFRi or PA/subject platinum-based compound combination as defined below, that will elicit the biological, physiological, pharmacological, therapeutic or medical response of a cell, tissue, system, body, animal, individual, patient or human that is being sought by the researcher, pharmacologist, pharmacist, veterinarian, medical doctor, or other clinician, e.g., lessening of the effects/symptoms of cell proliferative disorders such as a cancer or tumor, or killing or inhibiting growth of a proliferating cell, such as a tumor cell.

The term "contacted", "contacting", "brought into contact" and "exposed to", refers to any process, method or route of administration, by which a drug, a compound, or any combination of drugs or compounds, is brought into vicinity with a target cell, such as a cancer cell or a cell derived from a tumor, in such a way that the drug, compound or combination of drugs or compounds, can exert its action onto said target cell. Said action on said target cell is typically a growth inhibitory, an anti-proliferative or a cytotoxic action.

The term "further treated", "further administer" or "further administered", means that the different therapeutic agents may be administered together, subsequently, intermittently or one after the other. Such further administration may be temporally or spatially separated, for example at different times, on different days or via different modes or routes of administration.

The term "halogen" or "halo" refers to fluorine, chlorine, bromine and iodine.

The term "IC50", as used herein, refers to concentrations at which a measurable phenotype or response, for example growth of cells such as tumor cells, is inhibited by 50%. IC50 values can be estimated from an appropriate dose-response curve, for example by eye or by using appropriate curve fitting or statistical software. More accurately, IC50 values may be determined using non-linear regression analysis.

As used herein, an "individual" means a multi-cellular organism, for example an animal such as a mammal, preferably a primate. In addition to primates, such as humans, a variety of other mammals can be treated according to the method of the present invention. For example, mammals including, but not limited to, cows, sheep, goats, horses, dogs, cats, guinea pigs, rats or other bovine, ovine, equine, canine, feline, rodent or murine species can be used.

The term "metabolite", as used herein, refers to any substance produced by metabolism or by a metabolic process. Metabolism, as used herein, refers to the various physical/chemical/biochemical/pharmacological reactions involved in the transformation of molecules or chemical compounds occurring in the cell, tissue, system, body, animal, individual, patient or human therein. The term "metabolite" also includes a substance derived from a drug by physical, chemical, biological or biochemical processes in the body or cell after the drug is administered.

The term "prodrug", as used herein, refers to an agent which is converted into a pharmacologically active parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A prodrug may be converted into the parent drug by various mechanisms, including enzymatic processes and metabolic hydrolysis. See Gangwar et al., "Prodrug, molecular structure and percutaneous delivery", Des. Biopharm. Prop. Prodrugs Analogs, [Symp.] Meeting Date 1976, 409-21. (1977); Nathwani and Wood, "Penicillins: a current review of their clinical pharmacology and therapeutic use", Drugs 45(6): 866-94 (1993); Sinhababu and Thakker, "Prodrugs of anticancer agents", Adv. Drug Delivery Rev. 19(2): 241-273 (1996); Stella et al., "Prodrugs. Do they have advantages in clinical practice?", Drugs 29(5): 455-73 (1985); Tan et al. "Development and optimization of anti-HIV nucleoside analogs and prodrugs: A review of their cellular pharmacology, structure-activity relationships and pharmacokinetics", Adv. Drug Delivery Rev. 39(1-3): 117-151 (1999).

As used herein, a "proliferative disorder" includes a disease or disorder that affects a cellular growth, differentiation, or proliferation process. This term further includes a disorder affecting an animal in a manner which is marked by aberrant, or otherwise unwanted, proliferation of a subset of cells of an animal. Cancer and tumors are proliferative disorders. Cells comprising or derived from a tumor will generally be understood to be proliferating cells, typically hyper-proliferating cells, and in other circumstances, a tumor cell may be dysplastic, or may have proliferated. As used herein, a "cellular growth, differentiation or proliferation process" is a process by which a cell increases in number, size or content, by which a cell develops a specialized set of characteristics which differ from that of other cells, or by which a cell moves closer to or further from a particular location or stimulus. A cellular growth, differentiation, or proliferation process includes amino acid transport and degradation and other metabolic processes of a cell. A cellular proliferation disorder may be characterized by aberrantly regulated cellular growth, proliferation, differentiation, or migration. Cellular proliferation disorders include tumorigenic diseases or disorders. As used herein, a "tumorigenic disease or disorder" includes a disease or disorder characterized by aberrantly regulated cellular growth, proliferation, differentiation, adhesion, or migration, which may result in the production of or tendency to produce tumors. As used herein, a "tumor" includes a benign or malignant mass of tissue. Examples of cellular growth or proliferation disorders include, but are not limited to, cancer, e.g., carcinoma, sarcoma, or leukemia, examples of which include, but are not limited to, colon, ovarian, lung, breast, endometrial, uterine, hepatic, gastrointestinal, prostate, and brain cancer; tumorigenesis and metastasis; skeletal dysplasia; and hematopoietic and/or myeloproliferative disorders.

2. Platinum-based Compounds

In a particular embodiment the platinum-based chemotherapeutic agents to be used in accordance with the present invention are selected from:
(a) an orally available platinum-based chemotherapeutic agent;
(b) a platinum-based chemotherapeutic agent comprising a platinum (IV) co-ordination complex;
(c) a platinum-based chemotherapeutic agent represented by the following general structure:

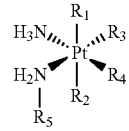

(formula I)

wherein $R_1$ and $R_2$ may be present or absent, each of $R_1$-$R_4$ is independently selected from halogen, hydroxyl, and acetate, and $R_5$ is a cycloalkyl;
(d) satraplatin or a metabolite of satraplatin;
or a pharmaceutically acceptable salt, isomer or prodrug of (a) to (d).

In another particular embodiment the platinum-based chemotherapeutic agents to be used in accordance with the present invention are selected from:
(a) an orally available platinum-based chemotherapeutic agent;
(b) a platinum-based chemotherapeutic agent represented by the following general structure:

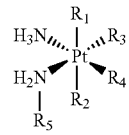

(formula I)

wherein $R_1$ and $R_2$ may be present or absent, each of $R_1$-$R_4$ is independently selected from halogen, hydroxyl, and acetate, and $R_5$ is a cycloalkyl;
(c) satraplatin or a metabolite of satraplatin;
or a pharmaceutically acceptable salt, isomer or prodrug of (a) to (c). In more particular embodiments said platinum-based compound are used in combination with an inhibitor of a receptor of the EGFR family.

In one embodiment of the present invention, the subject platinum-based compound is an orally available platinum chemotherapeutic agent. The phrase "orally available", as used herein, means that the drug or agent has biological, physiological, pharmacological, therapeutic, medically or clinically significant activity when administered orally. Suitable orally available platinum-based therapeutic agents include: satraplatin (JM216), JM118 and JM383 or a pharmaceutically acceptable salt, isomer or prodrug thereof, and others described in EP 0147926 and U.S. Pat. No. 5,072,011. Other orally available platinum-based therapeutic agents include ZD0473 (AMD473) and LA-12 ((OC-6-43)-bis(acetato)(1-adamantylamine)amminedichloroplatinum(IV)).

However, it should be recognised that although a platinum-based chemotherapeutic agent may be orally available, such agent may also be administered through other appropriate routes, such as rectal, intramuscular, intravenous, intraperitoneal, and subcutaneous, which administration would still be recognised as following the teaching of the instant invention.

In another embodiment, the platinum-based compound is a platinum (IV) co-ordinated compound, in which the oxidation state of the platinum is +4. Examples are satraplatin (JM216), JM518, JM559, JM383, iproplatin, tetraplatin (ormaplatin), LA-12 ((OC-6-43)-bis(acetato)(1-adamantylamine)amminedichloroplatinum(IV)), JM149, JM221, JM335 and the platinum (Pt) IV compounds disclosed in U.S. Pat. Nos. 6,413,953, 5,072,011, 5,519,155, 5,547,982, 6,518, 428, WO 01/76569 and WO 02/28871, and Coordination Chemistry Reviews (2002) 232, 49-67, the entirety of which are incorporated herein.

In a further embodiment, the platinum-based compound is a platinum compound of a structure represented by the following general formula (formula I):

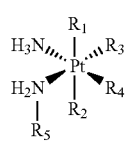

(formula I)

R1-R4 may be the same or different and are each independently selected from halogen, hydroxyl and acetate. R5 is a cycloalkyl, preferably a cyclohexyl. In certain embodiments, R1 and R2 are absent. In other embodiments, R1 and R2 are the same and are hydroxyl or acetate. In certain embodiments, R3 and R4 are the same and are both hydroxyl or preferably halogen, for example, chloride.

In yet another aspect of the invention, the platinum-based chemotherapeutic agent is satraplatin, or a metabolite of satraplatin. Satraplatin (JM216) has the structure:

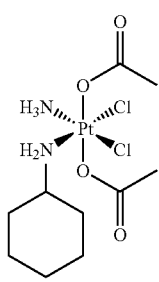

(formula IA)

In yet another aspect of the invention, the platinum-based chemotherapeutic agent is JM118. JM118 has the structure:

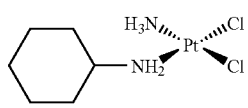

(formula II)

Satraplatin can be synthesised according to the method disclosed in U.S. Pat. Nos. 5,072,011 and 5,244,919 or by appropriate modification of the method disclosed in U.S. Pat. No. 6,518,428.

Upon administration of satraplatin to a cell, animal or a human patient, a number of related platinum-containing metabolites may be formed. FIG. 1 (taken from Raynaud et al. 1996 Cancer Chemother Phamacol 38:155-162) shows exemplary metabolites of satraplatin (JM216), and depicts JM118, JM383, JM518, JM559 and JM149. As will be appreciated by a person skilled in the art, additional platinum-containing molecules may be formed by metabolism of satraplatin after administration to a cell, animal or human patient, and such metabolites of satraplatin are encompassed in the scope of the instant invention. Suitable metabolites may be formed within the treated cell, animal or human by biological or biochemical biotransformation. Alternatively, such metabolites may be first formed out of the treated cell (such as in the GI tract), or may be formed by synthetic reaction from suitable starting materials and administered directly to the cell, animal or human patient. For example, JM118 may be synthesised according to the method disclosed in EP 147926, GB 2,060,615 and U.S. Pat. No. 4,329,299, or may be formed by biotransformation from JM216 in a separate fermentation step.

In a particular embodiment, the platinum-based compound is selected from satraplatin (JM216), JM118 and JM383 or a prodrug thereof. The term "prodrug", as used herein, also includes a substance that can give rise to a pharmacologically active metabolite. The prodrug itself may or may not be active; for example, it may be an inactive precursor. In some aspects of the invention the prodrug that is metabolised is satraplatin. In other aspects of the invention said platinum-based chemotherapeutic agent is a prodrug of a platinum-based chemotherapeutic agent, or a compound that is metabolised to a platinum-based chemotherapeutically active agent.

An exemplary subject platinum-based chemotherapeutic agent may be brought into contact, exposed to or administered directly to the cell, individual, animal or human patient. However, as will be evident from the discussion of metabolites, a first platinum-based compound may be brought into contact, exposed to or administered to a cell, whereafter an exemplary platinum-based chemotherapeutic agent may be formed by metabolism of the first platinum-based compound. Such first platinum-based compound so administered may be considered a 'prodrug' of the exemplary subject platinum-based chemotherapeutic agent. For example, JM518 may be considered a prodrug of JM118, as JM118 (an exemplary compound useful for the method of the invention) is formed by metabolism of JM518. Analogously, JM216 may also be considered a prodrug of JM118. Other compounds that when administered to a cell, animal, individual, patient or human, are converted (metabolised) to an exemplary compound useful for the methods of the invention, such as JM118, would be considered within the scope of the instant invention. Such other compounds, may include salts, esters or phosphates of the exemplary subject compound useful for the method of the invention, and following the disclosure of the instant invention, a person skilled in the art would be able to envision a number of appropriate such prodrug compounds.

In another embodiment, the platinum-based compound is an intermediate in the synthesis of satraplatin (JM216), JM118 and JM383. Exemplary intermediates include IP-118 (U.S. Pat. No. 4,687,780), JM118 (an intermediate for synthesizing satraplatin, EP 147926) and JM149 (EP 333351).

In particular embodiments the platinum-based compound is a compound which, after administration to an individual suffering from a cancer or a tumor, results in a compound of:

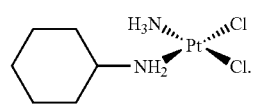

(formula II)

In yet another embodiment, the platinum-based compound is represented by one of the following general structures:

(A) Those disclosed in U.S. Pat. No. 5,072,011, represented by the following general structure:

1. A Pt(IV) anti-tumor complex of the formula

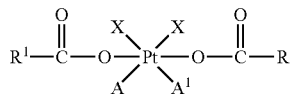

wherein A and A¹ are individually selected from the group consisting of $NH_3$ and an amino group of 1 to 10 carbon atoms, with the proviso that when both A and A¹ are amino groups, at least one is an amino group of 1 to 3 carbon atoms; both X groups are the same and are Cl or Br; R and R¹ are individually selected from the group consisting of $C_1$-$C_{10}$ alkyl, cycloalkyl, aryl, aralkyl of 3 to 7 carbon atoms, alkoxy, alkenyl, alkylamino of 1 to 6 carbon atoms wherein the group is joined to the carbonyl through the hetero-atom in the case of alkoxy and alkylamino, and H; such that the X groups are cis to each other and the $CO_2R$ and $CO_2R^1$ groups are trans to each other.

(B) Those disclosed in U.S. Pat. No. 5,244,919, represented by the following general structure:

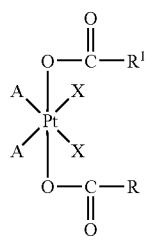
(I)

wherein A and A¹ are selected from the group consisting of $NH_{NH3}$ and an amino group; R and R¹ are hydrogen, $C_1$-$C_{10}$ alkyl alkenyl, aryl, aralkyl, alkylamino or alkoxy; and X is halogen or alkyl monocarboxylate or dicarboxylate.

(C) Those disclosed in U.S. Pat. No. 5,519,155, as represented by the general structure:

1. A Pt(IV) complex of general formula I,

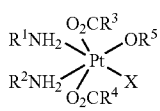
1 in which
X is a halide atom, a pseudohalide or hydroxy group,
R¹ and R² are hydrogen, $C_1$ to $C_6$ straight or branched chain alkyl or cyclo-alkyl, aryl or $R^1NH_2$ is a heterocyclic cyclic nitrogen donor, and R¹ and R² may be the same as or different from one another,
R³ and R⁴ are hydrogen, $C_1$ to $C_5$ straight or branched chain alkyl or cyclo-alkyl or aryl, and R³ and R⁴ may be the same as or different from one another, and p1 R⁵ is hydrogen, methyl or ethyl,
and having the cis, tuns, cis structure.

(D) Those disclosed EP 0 147 926 A1, as represented by the general structure:

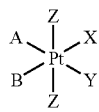

in which A and B are the same or different and are each selected from amine and alkylamines or together represent a diaminocyoalkane, X and Y are the same or different and are selected from halide and pseudohalide or together represent cycloalkanedicarboxylate, with the provisos that when X and Y together represent cycloalkanedicarboxylate A and B do not represents amine and/or alkylamine, when A and B together represent a diaminocyclohexane X end Y do not represent halide and/or pseudohalide, and when A represents amine B does not represent ethylamine, isopropylamine or cyclopentylamine and the Z moieties are optional and are selected from halide and hydroxy, in (E) Those disclosed in U.S. Pat. No. 5,547,982 as represented by the general structures:

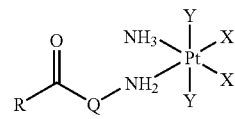
CLASS I

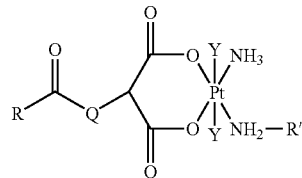
CLASS II

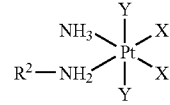
CLASS III wherein R is H, lower alkyl of up to 8 carbons, alkenyl or alkynyl of up to 8 carbons or aryl; X is Cl, malonate, glycolate or oxalate; Y is OH, Cl, $COOR^1$ Lens B, or absent; Q is an alkylene, alkenyl, alkynyl or aryl linking group; R' is H, lower alkyl or aryl; R' is H, aliphatic, aromatic or cyclo aliphatic group and R² is a cyclic aliphatic ketone, ketal, hemiacetal or acetal.

(F) Those disclosed in EB 0 727 430B1 as represented by the general structures:

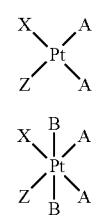
Ia

Ib where
each A is a leaving group and may be the same or different, or together form a bi-dentate carboxylate or sulphate,
each B, which may be the same or different, is halo, hydroxy, carboxylate, carbamate or carbonate ester.
Z is a substituted amine wherein the substituent sterically hinders access of the Pt atom to a DNA strand of a tumor cell, wherein Z is an unsaturated cyclic amine coordinated to Pt through the amine nitrogen atom, which cyclic amine may contain one or more other heteroatoms and wherein said Z has a substitutent on the atom adjacent the amine nitrogen atom and X is NH₃.

This includes the following compound, AMD473:

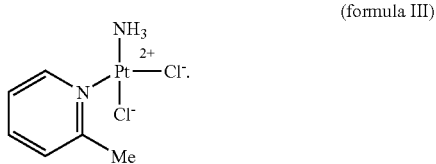

(formula III)

(G) Those disclosed in U.S. Pat. No. 4,329,299 as represented by the general structures:

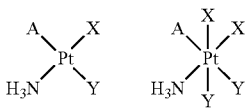

in which A is an amine having the formula R—NH₂ where R is branched chain alkyl, and X and Y are the same or different halogen.

(H) Those disclosed in WO 99/61451 as represented by the general structure:

1. A platinum complex with oxidation number IV of the general formula (I)

(I)

wherein
X represents a halogen atom,
B represent, independently to each other, a halogen atoms a hydroxyl group or a carboxylate group containing 1 to 6 carbon atoms, and
A represents a primary tricyclic amine containing 10 to 14 carbon atoms, which may be optionally substituted on the tricyclic ring by one or two alkyl group(s) each containing 1 to 4 carbon atoms, and, furthermore,
an inclusion complex of the above platinum complex with beta- or gamma-cyclodextrin which may be optionally substituted by hydroxyalkyl groups containing 1 to 6 carbon atoms.

This includes the following compound, LA-12:

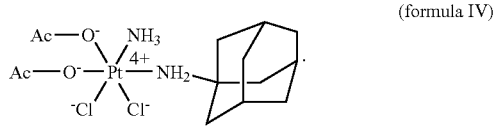

(formula IV)

In particular embodiments the platinum-based compound is represented by any one of the general structures (A)-(E) or (G)-(H) of the above list. In other particular embodiments the platinum-based compound is represented by any one of the general structures (A)-(H) when used in combination with an inhibitor of a receptor of the EGFR family.

The platinum-based compounds described above will be collectively referred herein as the "subject platinum-based compounds", "subject platinum-based chemotherapeutic agents" or simply "platinum-based compounds". The subject platinum-based compounds also encompass any such compounds in pharmaceutically acceptable salt forms. The subject platinum-based compounds of the invention may contain one or more asymmetric centers, preferably carbon or platinum, and thus occur as geometrical isomers or stereoisomers. The present invention encompasses all these isomers and mixtures thereof, as well as pharmaceutically acceptable salts and prodrugs or the subject platinum-based compounds.

3. Inhibitors of Receptors of the EGFR Family

Herein, it is demonstrated that inhibitors of receptors of the EGFR family (also referred to as "EGFRi") act synergistically with the subject platinum-based compounds. In particular we demonstrate that compounds that act on receptors of the EGFR family (also known as HER family, and including receptors EGFR1/HER1, EGFR2/HER2, EGFR3/HER3 and EGFR4/HER4) act synergistically with the subject platinum-based compounds. Furthermore, it is demonstrated that this synergistic action is not limited by nature of the compound which is administered with the subject platinum-based compound. Synergism was observed with antibodies, as well as with small molecule inhibitors. Therefore it is contemplated that all compounds, small molecules (as commonly understood by the skilled artisan), antibodies and agents that inhibit receptors of the EGFR family act synergistically with the subject platinum-based chemotherapeutic agents.

The family of the receptors of the EGFR family includes EGFR1 (endothelian growth factor receptor; ErbB1; HER1; encoded by erbB1), HER2 (EGFR2; encoded by erbB2), HER3 (EGFR3; encoded by erbB3) and HER4 (EGFR4; encoded by erbB4). This class of receptors is well known and described (see for example Int J Oncol (2003) 22, 237 and Clin Cancer Res (2005) 11, 7203). All these receptors are meant to be included in the term "receptors of the EGFR family". These receptors are also known cancer targets and various biologics, e.g. antibodies, and small molecule inhibitors were developed which inhibit receptors of the EGFR family.

Herceptin (trastuzumab) is a monoclonal antibody that binds HER2, a receptor that is found on tumor cells, such as breast cancer cells and lymphoma cells. It is mainly used to treat women with advanced breast cancer. Herceptin attaches to the HER2 protein so that EGF cannot bind to its receptor on the cancer cells. This stops the cells from dividing and growing. Herceptin also works by attracting the body's own immune cells to help destroy the cancer cells.

Other antibodies which bind HER2 include MAbs 4D5 (ATCC CRL 10463), 2C4 (ATCC HB-12697), 7F3 (ATCC HB-12216), and 7C2 (ATCC HB 12215) (see, U.S. Pat. No. 5,772,997; WO98/77797; and U.S. Pat. No. 5,840,525). Humanized anti-HER2 antibodies include huMAb4D5-1, huMAb4D5-2, huMAb4D5-3, huMAb4D5-4, huMAb4D5-6, huMAb4D5-7 and huMAb4D5-8 (HERCEPTIN®) as described in Table 3 of U.S. Pat. No. 5,821,337; humanized 520C9 (WO93/21319). Human anti-HER2 antibodies are described in U.S. Pat. No. 5,772,997 issued Jun. 30, 1998 and WO 97/00271 published Jan. 3, 1997. Other anti-HER2 antibodies include but are not limited to pertuzumab, 2C4, CB11, 300G9, E2-4001, CBE1, ICR12. Another antibody that binds to a receptor of the EGFR family is cetuximab (erbitux), and this antibody is particularly encompassed within the present invention.

All these antibodies are encompassed within the scope of the present invention and it is claimed that all antibodies that bind to inhibitors of receptors of the EGFR family act synergistically with the subject platinum-based chemotherapeutic agents. It is also contemplated that all antibodies that bind to the human receptors of the EGFR family, as for example those described in Semba et al., PNAS (USA) 82:6497-6501 (1985) and Yamamoto et al. Nature 319:230-234 (1986) (Genebank accession number X03363), and functional derivatives, such as amino acid sequence variants thereof, act synergistically with the subject platinum based chemotherapeutic agents.

Erlotinib (Tarceva) was approved in the United States for the treatment of non-small cell lung cancer (NSCLC) in November 2004 and Europe in September 2005. Other types of cancers in which erlotinib is tested include pancreatic cancer, ovarian cancer and cancer of the head and neck. Erlotinib binds to the epidermal growth factor receptor (EGFR) and thereby blocks the attachment of epidermal growth factor (EGF) and the activation of tyrosine kinase.

It is contemplated that erlotinib and derivatives of erlotinib, all of which are referred to as 'erlotinib' or 'Tarceva', are within the spirit of the present invention and act synergistically with the subject platinum-based compounds. Such compounds are described in WO 9630347, U.S. Pat. No. 5,747, 498, Drugs of the Future (2002), 27(10), 923-934 and Current Opinion in Investigational Drugs (PharmaPress Ltd.) (2002), 3(9), 1385-1395.

Other inhibitors of EGFR are contemplated as well, including Gefitinib (compound ZD1839 developed by AstraZeneca UK Ltd.; available under the trade name Iressa), ARRY-334543, 4-dimethylamino-but-2-enoic acid; 4-(3-chloro-4-fluoro phenylamino)-3-cyano-7-ethoxy-quinolin-6-yl-amide ("EKB-569", sometimes also referred to as "EKI-569", see for example WO/2005/018677 and Torrance et al., Nature Medicine, vol. 6, No. 9, September 2000, p. 1024) and/or HKI-272 or HKI-357 (Wyeth; see Greenberger et al., Proc. I Ith NCI EORTC-AACR Symposium on New Drugs in Cancer Therapy, Clinical Cancer Res. Vol. 6 Supplement, November 2000, ISSN 1078-0432; in Rabindran et al., Cancer Res. 64: 3958-3965 (2004); Holbro and Hynes, Ann. Rev. Pharm. Tox. 44:195-217 (2004); Tsou et al, J. Med. Chem. 205, 48, 1107-1131; and Tejpar et al., J. Clin. Oncol. ASCO Annual Meeting Proc. Vol. 22, No. 14S: 3579 (2004)).

4. Chemotherapeutically Active Pyrimidine Analogues

Pyrimidine analogues (also referred to as "PA") inhibit the biosynthesis of pyrimidine nucleotides and/or mimic certain metabolites of this pathway. This leads to an interference with vital cellular functions, such as synthesis or function of nucleic acids. This includes DNA synthesis, inhibition of RNA function and/or processing and synthesis of thymidylate. 5-fluorouracil (5-FU, 5-fluoruracil) and gemcitabine (di-fluorodeoxycytidine, 2',2'-difluorodeoxycytidine, dFdC, LY 188011, Gemzar) are two compounds falling into this class.

Gemcitabine is metabolized intracellularly to two active metabolites, gemcitabine diphosphate (dFdCDP) and gemcitabine triphosphate (dFdCTP). The cytotoxic effects of gemcitabine are exerted through incorporation of dFdCTP into DNA with the assistance of dFdCDP, resulting in inhibition of DNA synthesis and induction of apoptosis. Gemcitabine is a radiation-sensitizing agent, acting cell-cycle phase specific (S and G1/S-phases).

Gemcitabine, derivatives and processes for making these compounds are described in EP 0272891, GB 2136425, EP 0306190, EP 0329348, U.S. Pat. Nos. 5,612,474, 5,637,688, EP0719788B1, EP0779275A2, WO9721719A1, U.S. Pat. Nos. 5,808,048, 6,001,994 and 6,555,518. It is contemplated that all compounds disclosed in these patents and applications are encompassed in the term 'gemcitabine' and are within the scope of the present invention.

5-FU is widely used in the treatment of cancer, including metastatic carcinomas of the breast and the gastrointestinal tract, hepatoma, and cancer of the ovary, cervix, urinary bladder, prostate, pancreas and the oropharyngeal areas. Gemcitabine is mainly used for the treatment of non-small cell lung cancer, pancreatic, bladder and breast cancer.

In particular embodiments a patient in need thereof may also be administered a prodrug of a chemotherapeutically active pyrimidine analogue or a compound that is metabolised to a chemotherapeutically active pyrimidine analogue in the human body. The chemotherapeutically active pyrimidine analogue formed in the human body may be the only or one of several compounds formed in the human body by administering a respective prodrug to a patient in need thereof. Such compounds include for example capecitabine (Xeloda), and capecitabine is particularly meant to be included in the embodiments and claims of the present invention.

It is contemplated that all compounds of the above described mechanism of action, i.e. chemotherapeutically active pyrimidine analogues, are encompassed within the scope of the present invention, hereinafter referred to as "chemotherapeutically active pyrimidine analogue(s)", including but not limited to 5-fluorouracil, 5-fluorodeoxyuridine (floxuridine), 5-fluorodeoxyuridine monophosphate, cytosine arabinoside (cytarabine, AraC), 5-azacytidine, gemcitabin, capecitabine and those compounds listed in Expert review of anticancer therapy (2003), 3(5), 717-28 and Expert Review of Anticancer Therapy (2003), 3(5), 717-728.

5. Assays for Effectiveness of Treatment

In one embodiment, the platinum-based compounds of the present invention kill tumor cells when administered in combination with an inhibitor of a receptors of the EGFR family or a chemotherapeutically active pyrimidine analogues. Viability of a tumor cell can be determined by any methods known in the art. For example, one may use the colorimetric cytotoxicity assay described for anticancer drug screening in Shekan et al., J. Natl. Cancer. Inst. 82: 1107-12 (1990). For another example, one may determine the viability of a tumor cell by contacting the cell with a dye and viewing it under a microscope. Viable cells can be observed to have an intact membrane and do not stain, whereas dying or dead cells having "leaky" membranes do stain. Incorporation of the dye by the cell indicates the death of the cell. A dye useful for this purpose is trypan blue.

The exemplary inhibitors of receptors of the EGFR family and chemotherapeutically active pyrimidine analogues and the platinum-containing composition of the present invention may induce cell death, for example by inducing necrosis or by inducing apoptosis, a mode of cell death, in resistant tumor cells. Apoptosis is recognized by a characteristic pattern of morphological, biochemical and molecular changes. Cells going through apoptosis appear shrunken and rounded. They also can be observed to become detached from a culture dish in which they are maintained. The morphological changes involve a characteristic pattern of condensation of chromatin and cytoplasm which can be readily identified by microscopy. When stained with a DNA-binding dye, e.g., H33258 or propidium iodide, apoptotic cells display classic condensed and punctuate nuclei instead of homogenous and round nuclei.

A typical characteristic of apoptosis is endonucleolysis, a molecular change in which nuclear DNA is initially degraded at the linker sections of nucleosomes to give rise to fragments equivalent to single and multiple nucleosomes. When these DNA fragments are subjected to gel electrophoresis, they reveal a series of DNA bands which are positioned approximately equally distant from each other on the gel. The size difference between the two bands next to each other is about the length of one nucleosome, i.e., 120 base pairs. This characteristic display of the DNA bands is called a DNA ladder and it indicates apoptosis of the cell. Apoptotic cells can also be identified by flow cytometric methods based on measurement of cellular DNA content, increased sensitivity of DNA to denaturation, or altered light scattering properties. These methods are well known in the art. It should be recognized however, that modes of programmed cell death, including apoptosis, may be following a number of mechanisms or show other phenotypes/properties to those described above. In such cases, these mechanisms may also be characterized, classified or considered as "apoptosis".

Cytotoxicity may also be measured using the SRB assay according to Shekan et al (J Natl Cancer Inst (1990) 82, 1107-112), as described in the Examples.

Additional assays for cell viability are described in Chapter 15 of Handbook of Fluorescent Probes and Research Products (Molecular Probes Handbook), which is incorporated in its entirety herein.

In one embodiment, the subject invention comprises a method of killing or inhibiting the growth of a tumor cell comprising contacting said cell with an effective amount of (a) an inhibitor of a receptor of the EGFR family or a chemotherapeutically active pyrimidine analogue, and (b) satraplatin or JM118. The growth inhibition and/or cell death of said tumor cells can be either partial (slowing down cell growth) or complete inhibition (i.e., arresting cells at a certain point in cell cycle). Cell growth can be measured by any techniques known in the art. Such techniques include, for example, MTT assay (based on reduction of the tetrazolium salt 3, [4,5-dimethylthiazol-2-yl]-2,5-diphenyletrazolium bromide), and PicoGreen assay using the DNA-binding dye Picogreen, both of which are described in Torrance, et al., Nat. Biotech. 19:940-945 (2001), incorporated herein in its entirety. Other assays for cell proliferation/growth are described in Chapter 15 of Handbook of Fluorescent Probes and Research Products (Molecular Probes Handbook).

Progression of disease, cancer or tumor in response to treatment can be monitored using any standard technique known in the art. For example, tumor size can be monitored and assessed to see if tumor size reduction has occurred as a result of the treatment. Monitoring and assessment may be aided by a variety of means including biopsies, manual inspection, microscopy, whole or partial body imaging and scans, and various molecular-based diagnostic and prognostic methods including those that investigate tumor-specific markers or mutations.

6. Tumors and Other Proliferative Disorders

The EGFRi or PA/subject platinum-based compound combination is useful to treat proliferative disorders. The term "proliferative disorder" is art-recognized and further includes a disorder affecting an animal in a manner which is marked by aberrant, or otherwise unwanted, proliferation of a subset of cells of an animal. Cancer and tumors are proliferative disorders. Cells comprising or derived from a tumor will generally be understood to be proliferating cells, typically a hyper-proliferating cell, and in other circumstances, a tumor cell may be dysplastic, or may have proliferated.

It will be apparent to a person skilled in the art, on reading the disclosure of the instant invention, that the methods, pharmaceutical compositions and packaged pharmaceuticals comprising the EGFRi or PA/subject platinum-based compound combination will be useful for the treatment of other proliferative disorders, or for killing or inhibiting proliferating cells including tumor cells.

Any tumors may benefit from treatment with the methods, uses, pharmaceutical compositions, packaged pharmaceuticals and kits of the present invention. Suitable tumors may be solid tumors, which are cancer of body tissues other than blood, bone marrow, or the lymphatic system, such as carcinomas and sarcomas. Suitable tumors may also be hematological tumors, such as leukemia and lymphomas. Leukemia is a collective term for malignant diseases characterized by a proliferation of malignantly changed white blood cells. Diseases arising from lymphatic tissue are called lymphomas.

Solid tumors may be selected from: liver cancer, stomach cancer, colon cancer, breast cancer, pancreas cancer, prostate cancer, skin cancer, renal cancer, bone cancer, skin cancer, cervical cancer, ovarian cancer, lung cancer, gynaecological cancers, urological and male genital cancers, soft tissue sarcomas, cancer of the major digestive glands, cancer of the bile duct, gall bladder cancer, bladder cancer, testicular cancer, cancers of the central nervous system, bronchial cancer, small and non-small-cell lung cancer, gastric cancer, and head and neck cancer. In some embodiments prostate cancer may be hormone-refractory prostate cancer.

Suitable tumors may also be hematological tumors. Hematological tumors may be leukemia, such as Acute Myelogenous Leukemia (AML), Acute Lymphoblastic Leukemia (ALL), Acute Leukemia, Acute Promyelocytic Leukemia, Chronic Granulocytic Leukemia (CGL), Chronic Leukemia, Chronic Lymphocytic Leukemia (CLL), Chronic Myelogenous Leukemia (CML), Chronic Myelomonocytic Leukemia, Common-type Acute Lymphoblastic Leukemia, Eosinophilic Leukemia, Erythroleukemia, Extranodal Lymphoma, Follicular Lymphoma, Hairy Cell Leukemia, Monocytic Leukemia, and Prolymphocytic Leukemia.

Hematological tumors may also be lymphoma, such as B Cell Lymphomas, Burkitt Lymphoma, Cutaneous T Cell Lymphoma, High-Grade Lymphoma, Hodgkin Lymphoma, Non-Hodgkin Lymphoma, Low-grade Lymphoma, Lymphoblastic Lymphoma, Mantle Cell Lymphoma, Marginal Zone Lymphoma, Mucosa-Associated Lymphoid Tissue (MALT) Lymphomas, T Cell Lymphomas, peripheral T cell lymphoma, multiple myeloma, Essential Thrombocythemia, Extramedullary myeloma, and Granulocytic Sarcomae.

The subject platinum-based compounds are also believed useful in treating other types of proliferative disorders, including, proliferative disorders which are characterized by benign indications. Such disorders may also be known as "cytoproliferative" or "hyperproliferative" in that cells are made by the body at an atypically elevated rate. Such disorders include, but are not limited to, the following: hemangiomatosis in new born, secondary progressive multiple sclerosis, chronic progressive myelodegenerative disease, neurofibromatosis, ganglioneuromatosis, keloid formation, Paget's disease of the bone, fibrocystic disease of the breast, Peronies and Duputren's fibrosis, restenosis and cirrhosis.

7. Combination Therapy, Pharmaceutical Formulations and Dosages

The present invention provides various aspects relating to a method of prevention and/or treatment of a cancer or a tumor, and in particular to a combination therapy, methods, compositions and pharmaceutical packages comprising an inhibitor of a receptor of the EGFR family or a chemotherapeutically active pyrimidine analogue and a subject platinum-based compound selected from:

(a) an orally available platinum-based chemotherapeutic agent;
(b) a platinum-based chemotherapeutic agent comprising a platinum (IV) co-ordination complex;
(c) a platinum-based chemotherapeutic agent represented by the following general structure:

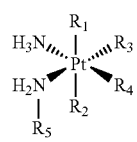

(formula I)

wherein $R_1$ and $R_2$ may be present or absent, each of $R_1$-$R_4$ is independently selected from halogen, hydroxyl, and acetate, and $R_5$ is a cycloalkyl;
(d) satraplatin or a metabolite of satraplatin;
or a pharmaceutically acceptable salt, isomer or prodrug of (a) to (d). Various methods, uses, therapeutic combinations, pharmaceutical compositions, packaged pharmaceuticals, formulations and kits are encompassed within the present invention which are based on this combination, and which are referred to as "EGFRi or PA/subject platinum-based compound combination", "subject combination therapy" or "subject compound combination".

The EGFRi or PA/subject platinum-based compound combination can be co-administered, e.g., in the same or different formulation. The term "co-administer" or "co-administered", as used herein, include administering two or more different therapeutic agents concurrently, sequentially or intermittently in all of the various aspects of the method of the invention. Thus, the subject platinum-based compounds or the EGFRi or PA/subject platinum-based compound combination may be administered before, after, or together with another chemotherapeutic agent or another pharmacological active agent to an individual in need thereof. The methods of the present invention can also be combined with other methods of cancer treatment, such as radiation therapy, surgery, or immunotherapy. In one embodiment the subject platinum-based compound is administered before the inhibitor of a receptor of the EGFR family or the chemotherapeutically active pyrimidine analogue. In another embodiment the receptor of the EGFR family or the chemotherapeutically active pyrimidine analogue is administered before the subject platinum-based compound.

As shown in the Examples, Applicants have demonstrated that exemplary subject platinum-based compounds, including satraplatin (JM216) and JM118, in combination with an inhibitor of a receptor of the EGFR family or a chemotherapeutically active pyrimidine analogue, act highly synergistic, in particularly when administered in a certain order. Thus, one embodiment of the present invention relates to methods of treating an individual suffering from a tumor or a cancer by administering to the individual an effective amount of (a) an inhibitor of a receptor of the EGFR family, and (b) satraplatin or JM118. Another embodiment of the present invention relates to methods of treating an individual suffering from a tumor or a cancer by administering to the individual an effective amount of (a) a chemotherapeutically active pyrimidine analogue, and (b) satraplatin or JM118. In certain embodiments an inhibitor of a receptor of the EGFR family is administered first. In other embodiments a chemotherapeutically active pyrimidine analogues administered first. In yet other embodiments satraplatin or JM118 is administered first.

In other embodiments the present invention provides a packaged pharmaceutical comprising (i) a first pharmaceutical composition containing a subject platinum-based chemotherapeutic agent selected from:
(a) an orally available platinum-based chemotherapeutic agent;
(b) a platinum-based chemotherapeutic agent comprising a platinum (IV) co-ordination complex;
(c) a platinum-based chemotherapeutic agent represented by the following general structure:

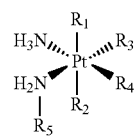

(formula I)

wherein $R_1$ and $R_2$ may be present or absent, each of $R_1$-$R_4$ is independently selected from halogen, hydroxyl, and acetate, and $R_5$ is a cycloalkyl;
(d) satraplatin or a metabolite of satraplatin;
or a pharmaceutically acceptable salt, isomer or prodrug of (a) to (d); and
(ii) instructions to administer, to an individual suffering from a cancer or a tumor, said first pharmaceutical composition and a second pharmaceutical composition containing an inhibitor of a receptor of the EGFR family or a chemotherapeutically active pyrimidine analogue,
wherein said platinum based chemotherapeutic agent is, or on administration results in, a compound having the structure of:

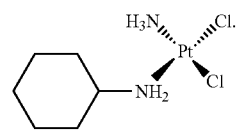

(formula II)

In particular embodiments said inhibitor of a receptor of the EGFR family is herceptin or erlotinib and/or said subject platinum-based chemotherapeutic agent is satraplatin or JM118. In other embodiments said pyrimidine analogue is gemcitabine, capecitabine or 5FU and/or said subject platinum-based chemotherapeutic agent is satraplatin or JM118. In other particular embodiments said subject platinum-based chemotherapeutic agent is satraplatin.

In other embodiments the present invention provides a packaged pharmaceutical comprising a first pharmaceutical composition containing an inhibitor of a receptor of the EGFR family or a chemotherapeutically active pyrimidine analogue, wherein said packaged pharmaceutical further comprises instructions to administer, to an individual suffering from a cancer or a tumor, said first pharmaceutical composition and a second pharmaceutical composition containing a subject platinum-based chemotherapeutic agent selected from:
(a) an orally available platinum-based chemotherapeutic agent;
(b) a platinum-based chemotherapeutic agent comprising a platinum (IV) co-ordination complex;
(c) a platinum-based chemotherapeutic agent represented by the following general structure:

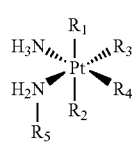

(formula I)

wherein $R_1$ and $R_2$ may be present or absent, each of $R_1$-$R_4$ is independently selected from halogen, hydroxyl, and acetate, and $R_5$ is a cycloalkyl;
(d) satraplatin or a metabolite of satraplatin;
or a pharmaceutically acceptable salt, isomer or prodrug of (a) to (d); wherein said chemotherapeutic agent is, or on administration results in, a compound having the structure of:

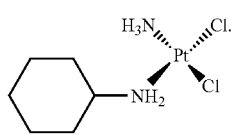

(formula II)

In a particular embodiment the invention provides a packaged pharmaceutical comprising:
(a) a first pharmaceutical composition containing a platinum-based chemotherapeutic agent; and
(b) instructions to administer, to an individual suffering from a cancer or a tumor, said first pharmaceutical composition and a second pharmaceutical composition containing an inhibitor of a receptor of the EGFR family or a chemotherapeutically active pyrimidine analogue within about 14 days of each other,
wherein said platinum-based chemotherapeutic agent is, or on administration results in, a compound having the structure of:

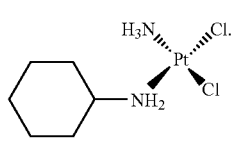

(formula II)

In other particular embodiment the invention provides a packaged pharmaceutical comprising a first pharmaceutical composition containing an inhibitor of a receptor of the EGFR family or a chemotherapeutically active pyrimidine analogue, wherein said packaged pharmaceutical further comprises instructions to administer, to an individual suffering from a cancer or a tumor, said first pharmaceutical composition and a second pharmaceutical composition containing a platinum-based chemotherapeutic agent within about 14 days of each other, wherein said platinum-based chemotherapeutic agent is, or on administration results in, a compound having the structure of:

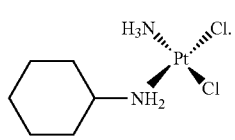

(formula II)

Most preferred are packaged pharmaceuticals wherein said platinum-based chemotherapeutic agent is a compound having the structure of:

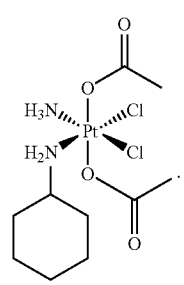

(formula IA)

In particular embodiments said inhibitor of a receptor of the EGFR family is herceptin or erlotinib and/or said subject platinum-based chemotherapeutic agent is satraplatin or JM118. In other embodiments said chemotherapeutically active pyrimidine analogue is gemcitabine, capecitabine or 5FU and/or said subject platinum-based chemotherapeutic agent is satraplatin or JM118. In other particular embodiments said subject platinum-based chemotherapeutic agent is satraplatin.

In very particular embodiments a compound having the structure of:

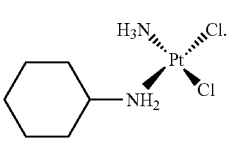

(formula II)

is formed in a patient in need thereof after a subject platinum-based chemotherapeutic agent selected from:
(a) an orally available platinum-based chemotherapeutic agent;
(b) a platinum-based chemotherapeutic agent comprising a platinum (IV) co-ordination complex;
(c) a platinum-based chemotherapeutic agent represented by the following general structure:

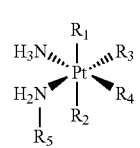

(formula I)

wherein $R_1$ and $R_2$ may be present or absent, each of $R_1$-$R_4$ is independently selected from halogen, hydroxyl, and acetate, and $R_5$ is a cycloalkyl;
(d) satraplatin or a metabolite of satraplatin;
or a pharmaceutically acceptable salt, isomer or prodrug of (a) to (d);
is administered to said patient. The compound of formula II is formed within the human or animal body, for example by metabolic processes. It is stressed that it is well known in the art that the administration of satraplatin (formula IA) leads to the formation of JM-118 (formula II). This feature may be combined with any other embodiment or claim of the present invention.

In other embodiments the present invention provides methods for killing or inhibiting the growth of a tumor cell comprising contacting said cell with an effective amount of (a) an inhibitor of a receptor of the EGFR family or a chemotherapeutically active pyrimidine analogue, and (b) a subject platinum-based chemotherapeutic agent selected from:
(a) an orally available platinum-based chemotherapeutic agent;
(b) a platinum-based chemotherapeutic agent comprising a platinum (IV) co-ordination complex;
(c) a platinum-based chemotherapeutic agent represented by the following general structure:

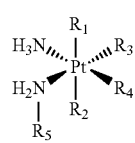

(formula I)

wherein $R_1$ and $R_2$ may be present or absent, each of $R_1$-$R_4$ is independently selected from halogen, hydroxyl, and acetate, and $R_5$ is a cycloalkyl;
(d) satraplatin or a metabolite of satraplatin;
or a pharmaceutically acceptable salt, isomer or prodrug of (a) to (d). In particular embodiments said inhibitor of a receptor of the EGFR family is herceptin or erlotinib and/or said subject platinum-based chemotherapeutic agent is satraplatin or JM118. In certain embodiments herceptin or erlotinib is contacted with said cell first. In other particular embodiments said chemotherapeutically active pyrimidine analogue is gemcitabine, capecitabine or 5FU and/or said subject platinum-based chemotherapeutic agent is satraplatin or JM118. In particular embodiments gemcitabine, capecitabine or 5FU is contacted with said cell first. In yet other embodiments satraplatin or JM118 is contacted with said cell first.

In other embodiments the present invention provides the use of a subject platinum-based chemotherapeutic agent selected from:
(a) an orally available platinum-based chemotherapeutic agent;
(b) a platinum-based chemotherapeutic agent comprising a platinum (IV) co-ordination complex;
(c) a platinum-based chemotherapeutic agent represented by the following general structure:

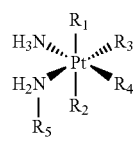

(formula I)

wherein $R_1$ and $R_2$ may be present or absent, each of $R_1$-$R_4$ is independently selected from halogen, hydroxyl, and acetate, and $R_5$ is a cycloalkyl;
(d) satraplatin or a metabolite of satraplatin;
or a pharmaceutically acceptable salt, isomer or prodrug of (a) to (d), for the preparation of a first pharmaceutical composition for use in the treatment of an individual suffering from a cancer or a tumor, wherein said first pharmaceutical composition is administered within about 14 days of administration of a second pharmaceutical composition containing an inhibitor of a receptor of the EGFR family or a chemotherapeutically active pyrimidine analogue. In particular embodiments said inhibitor of a receptor of the EGFR family is herceptin or erlotinib and/or said subject platinum-based chemotherapeutic agent is satraplatin or JM118. In other embodiments said pyrimidine analogue is gemcitabine, capecitabine or 5FU and/or said subject platinum-based chemotherapeutic agent is satraplatin or JM118.

In yet other embodiments the present invention provides the use of an inhibitor of a receptor of the EGFR family or a chemotherapeutically active pyrimidine analogue for the preparation of a first pharmaceutical composition for use in the treatment of an individual suffering from a cancer or a tumor, wherein said first pharmaceutical composition is administered within about 14 days of administration of a second pharmaceutical composition containing a subject platinum-based chemotherapeutic agent selected from:
(a) an orally available platinum-based chemotherapeutic agent;
(b) a platinum-based chemotherapeutic agent comprising a platinum (IV) co-ordination complex;
(c) a platinum-based chemotherapeutic agent represented by the following general structure:

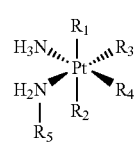

(formula I)

wherein $R_1$ and $R_2$ may be present or absent, each of $R_1$-$R_4$ is independently selected from halogen, hydroxyl, and acetate, and $R_5$ is a cycloalkyl;
(d) satraplatin or a metabolite of satraplatin;
or a pharmaceutically acceptable salt, isomer or prodrug of (a) to (d). In particular embodiments said inhibitor of a receptor of the EGFR family is herceptin or erlotinib and/or said subject platinum-based chemotherapeutic agent is satraplatin or JM118. In other embodiments said chemotherapeutically active pyrimidine analogue is gemcitabine, capecitabine or 5FU and/or said subject platinum-based chemotherapeutic agent is satraplatin or JM118.

In yet other embodiments the present invention provides an inhibitor of a receptor of the EGFR family or a chemotherapeutically active pyrimidine analogue for use in the treatment or prevention of a cancer or a tumor, wherein said inhibitor of a receptor of the EGFR family or said chemotherapeutically active pyrimidine analogue is administered with a subject platinum-based chemotherapeutic agent within about 14 days of each other. In yet other embodiments the present invention provides a subject platinum-based chemotherapeutic agent for use in the treatment or prevention of a cancer or a tumor, wherein said subject platinum-based chemotherapeutic agent is administered with an inhibitor of a receptor of the EGFR family or a chemotherapeutically active pyrimidine analogue within about 14 days of each other. In particular embodiments said inhibitor of a receptor of the EGFR family is herceptin or erlotinib and/or said subject platinum-based chemotherapeutic agent is satraplatin or JM118. In other embodiments said chemotherapeutically active pyrimidine analogue is gemcitabine, capecitabine or 5FU and/or said subject platinum-based chemotherapeutic agent is satraplatin or JM118.

In yet other embodiments the present invention provides the use of a platinum-based chemotherapeutic agent for the preparation of a first pharmaceutical composition for the treatment of an individual suffering from a cancer or a tumor, wherein said first pharmaceutical composition is administered within about 14 days of administration of a second pharmaceutical composition containing an inhibitor of a receptor of the EGFR family or a chemotherapeutically active pyrimidine analogue and wherein said platinum-based chemotherapeutic agent is, or on administration results in, a compound of formula II. In another embodiment the invention provides the use of an inhibitor of a receptor of the EGFR family or a chemotherapeutically active pyrimidine analogue for the treatment of an individual suffering from a cancer or a tumor, wherein said first pharmaceutical composition is administered within about 14 days of administration of a second pharmaceutical composition containing a platinum-based chemotherapeutic agent and wherein said platinum-based chemotherapeutic agent is, or on administration results in, a compound of formula II. In particular embodiments said inhibitor of a receptor of the EGFR family is herceptin or erlotinib and/or said subject platinum-based chemotherapeutic agent is satraplatin or JM118. In other embodiments said chemotherapeutically active pyrimidine analogue is gemcitabine, capecitabine or 5FU and/or said subject platinum-based chemotherapeutic agent is satraplatin or JM118.

In other embodiments the present invention provides the use of a platinum-based chemotherapeutic agent for the preparation of a first pharmaceutical composition for the treatment of an individual suffering from a cancer or a tumor, wherein said treatment is a combination treatment comprising said first pharmaceutical composition and a second pharmaceutical composition comprising an inhibitor of a receptor of the EGFR family or a chemotherapeutically active pyrimidine analogue, wherein said pharmaceutical compositions are administered within about 14 days of each other and wherein said platinum-based chemotherapeutic agent is, or on administration results in, a compound of formula II. In yet other embodiments the invention provides the use of an inhibitor of a receptor of the EGFR family or a chemotherapeutically active pyrimidine analogue for the preparation of a first pharmaceutical composition for the treatment of an individual suffering from a cancer or a tumor, wherein said treatment is a combination treatment comprising said first pharmaceutical composition and a second pharmaceutical composition comprising a platinum-based chemotherapeutic agent, wherein said pharmaceutical compositions are administered within about 14 days of each other and wherein said platinum-based chemotherapeutic agent is, or on administration results in, a compound of formula II. In particular embodiments said inhibitor of a receptor of the EGFR family is herceptin or erlotinib and/or said subject platinum-based chemotherapeutic agent is satraplatin or JM118. In other embodiments said chemotherapeutically active pyrimidine analogue is gemcitabine, capecitabine or 5FU and/or said subject platinum-based chemotherapeutic agent is satraplatin or JM118.

In other embodiments the present invention provides a first pharmaceutical composition comprising a subject platinum-based chemotherapeutic agent as defined above, prepared according to the use described in the preceding paragraphs, included in a pharmaceutical package further including instructions to administer, to an individual suffering from a cancer or a tumor, said first pharmaceutical composition and said second pharmaceutical recited in the preceding paragraphs within about 14 days of each other.

In particular embodiments the invention provides a first pharmaceutical composition prepared according to the use described in the preceding paragraphs, included in a pharmaceutical package further including instructions to administer, to an individual suffering from a cancer or a tumor, said first pharmaceutical composition and a second pharmaceutical composition comprising an inhibitor of a receptor of the EGFR family or a chemotherapeutically active pyrimidine analogue within about 14 days of each other. In other particular embodiments the invention provides a first pharmaceutical composition prepared according to the use described above, included in a pharmaceutical package further including instructions to administer, to an individual suffering from a cancer or a tumor, said first pharmaceutical composition and a second pharmaceutical composition comprising a platinum-based chemotherapeutic agent within about 14 days of each other. In other embodiments the present invention provides a first pharmaceutical composition comprising an inhibitor of a receptor of the EGFR family or a chemotherapeutically active pyrimidine analogue as defined above, prepared according to the use described in the preceding paragraphs, included in a pharmaceutical package further including instructions to administer, to an individual suffering from a cancer or a tumor, said first pharmaceutical composition and said second pharmaceutical recited in the preceding paragraphs within about 14 days of each other. In particular embodiments said inhibitor of a receptor of the EGFR family is herceptin or erlotinib and/or said subject platinum-based chemotherapeutic agent is satraplatin or JM118. In other embodiments said chemotherapeutically active pyrimidine analogue is gemcitabine, capecitabine or 5FU and/or said subject platinum-based chemotherapeutic agent is satraplatin or JM118.

In other embodiments the present invention provides a therapeutic combination for the treatment or prevention of a cancer or a tumor, including (a) an inhibitor of a receptor of the EGFR family or a chemotherapeutically active pyrimidine analogue and (b) a subject platinum-based chemotherapeutic agent selected from:
(a) an orally available platinum-based chemotherapeutic agent;
(b) a platinum-based chemotherapeutic agent comprising a platinum (IV) co-ordination complex;
(c) a platinum-based chemotherapeutic agent represented by the following general structure:

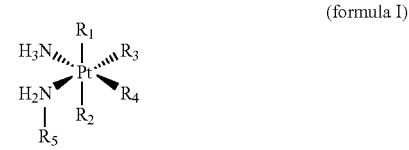

(formula I)

wherein $R_1$ and $R_2$ may be present or absent, each of $R_1$-$R_4$ is independently selected from halogen, hydroxyl, and acetate, and $R_5$ is a cycloalkyl;
(d) satraplatin or a metabolite of satraplatin;
or a pharmaceutically acceptable salt, isomer or prodrug of (a) to (d). In particular embodiments said inhibitor of a receptor of the EGFR family is herceptin or erlotinib and/or said subject platinum-based chemotherapeutic agent is satraplatin or JM118. In other embodiments said chemotherapeutically active pyrimidine analogue is gemcitabine, capecitabine or 5FU and/or said subject platinum-based chemotherapeutic agent is satraplatin or JM118.

In other embodiments the present invention provides a pharmaceutical composition for the treatment or prevention of a cancer or a tumor, including (a) an inhibitor of a receptor of the EGFR family or a chemotherapeutically active pyrimidine analogue and (b) a subject platinum-based chemotherapeutic agent selected from:
(a) an orally available platinum-based chemotherapeutic agent;

(b) a platinum-based chemotherapeutic agent comprising a platinum (IV) co-ordination complex;
(c) a platinum-based chemotherapeutic agent represented by the following general structure:

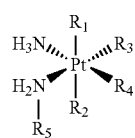

(formula I)

wherein $R_1$ and $R_2$ may be present or absent, each of $R_1$-$R_4$ is independently selected from halogen, hydroxyl, and acetate, and $R_5$ is a cycloalkyl;
(d) satraplatin or a metabolite of satraplatin;
or a pharmaceutically acceptable salt, isomer or prodrug of (a) to (d). In particular embodiments said inhibitor of a receptor of the EGFR family is herceptin or erlotinib and/or said subject platinum-based chemotherapeutic agent is satraplatin or JM118. In other embodiments said chemotherapeutically active pyrimidine analogue is gemcitabine, capecitabine or 5FU and/or said subject platinum-based chemotherapeutic agent is satraplatin or JM118.

The present invention also provides a packaged pharmaceutical comprising a first pharmaceutical composition of a subject platinum-based chemotherapeutic agent selected from:
(a) an orally available platinum-based chemotherapeutic agent;
(b) a platinum-based chemotherapeutic agent comprising a platinum (IV) co-ordination complex;
(c) a platinum-based chemotherapeutic agent represented by the following general structure:

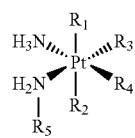

(formula I)

wherein $R_1$ and $R_2$ may be present or absent, each of $R_1$-$R_4$ is independently selected from halogen, hydroxyl, and acetate, and $R_5$ is a cycloalkyl;
(d) satraplatin or a metabolite of satraplatin;
or a pharmaceutically acceptable salt, isomer or prodrug of (a) to (d),
wherein said packaged pharmaceutical further comprises instructions to administer, to an individual suffering from a cancer or a tumor, said first pharmaceutical composition and a second pharmaceutical composition containing an inhibitor of a receptor of the EGFR family or a chemotherapeutically active pyrimidine analogue within about 14 days of each other. In particular embodiments said inhibitor of a receptor of the EGFR family is herceptin or erlotinib and/or said subject platinum-based chemotherapeutic agent is satraplatin or JM118. In other embodiments said chemotherapeutically active pyrimidine analogue is gemcitabine, capecitabine or 5FU and/or said subject platinum-based chemotherapeutic agent is satraplatin or JM118.

The present invention also provides a packaged pharmaceutical comprising a first pharmaceutical composition containing an inhibitor of a receptor of the EGFR family or a chemotherapeutically active pyrimidine analogue, wherein said packaged pharmaceutical further comprises instructions to administer, to an individual suffering from a cancer or a tumor, said first pharmaceutical composition and a second pharmaceutical composition containing a subject platinum-based chemotherapeutic agent selected from:
(a) an orally available platinum-based chemotherapeutic agent;
(b) a platinum-based chemotherapeutic agent comprising a platinum (IV) co-ordination complex;
(c) a platinum-based chemotherapeutic agent represented by the following general structure:

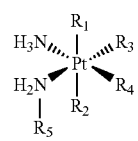

(formula I)

wherein $R_1$ and $R_2$ may be present or absent, each of $R_1$-$R_4$ is independently selected from halogen, hydroxyl, and acetate, and $R_5$ is a cycloalkyl;
(d) satraplatin or a metabolite of satraplatin;
or a pharmaceutically acceptable salt, isomer or prodrug of (a) to (d), within about 14 days of each other. In particular embodiments said inhibitor of a receptor of the EGFR family is herceptin or erlotinib and/or said subject platinum-based chemotherapeutic agent is satraplatin or JM118. In other embodiments said chemotherapeutically active pyrimidine analogue is gemcitabin or 5FU and/or said subject platinum-based chemotherapeutic agent is satraplatin or JM118.

The packaged pharmaceutical of the present invention may comprise instructions, or may provide otherwise, for the administration of one of said compounds to said individual at least 1 day, 2 days, 3 days, 5 days, 7 days, 10 days, or 14 days, before the other compound is administered to said individual. Hence, in certain embodiments said instructions provide for the sequential administration of the inhibitor of a receptor of the EGFR family or the chemotherapeutically active pyrimidine analogue and said subject platinum-based compound. In particular embodiments said inhibitor of a receptor of the EGFR family or the chemotherapeutically active pyrimidine analogue is administered to said individual 1 day, 2 days, 3 days, 5 days, 7 days, 10 days, or 14 days before said subject platinum-based compounds are administered to said individual. In other particular embodiments said subject platinum-based compound is administered to said individual 1 day, 2 days, 3 days, 5 days, 7 days, 10 days, or 14 days before said inhibitor of a receptor of the EGFR family or the chemotherapeutically active pyrimidine analogue is administered to said individual.

The present invention also provides for the use of a subject platinum-based chemotherapeutic agent selected from:
(a) an orally available platinum-based chemotherapeutic agent;
(b) a platinum-based chemotherapeutic agent comprising a platinum (IV) co-ordination complex;
(c) a platinum-based chemotherapeutic agent represented by the following general structure:

(formula I)

wherein $R_1$ and $R_2$ may be present or absent, each of $R_1$-$R_4$ is independently selected from halogen, hydroxyl, and acetate, and $R_5$ is a cycloalkyl;
(d) satraplatin or a metabolite of satraplatin;
or a pharmaceutically acceptable salt, isomer or prodrug of (a) to (d), in the manufacture of an anti-proliferative agent in a pharmaceutical package together with instructions for its use in combination with an inhibitor of a receptor of the EGFR family or the chemotherapeutically active pyrimidine analogue in the treatment of a cancer or a tumor. It also provides for the use of an inhibitor of a receptor of the EGFR family or the chemotherapeutically active pyrimidine analogue in the manufacture of an anti-proliferative agent in a pharmaceutical package together with instructions for its use in combination with a subject platinum-based chemotherapeutic agent selected from:
(a) an orally available platinum-based chemotherapeutic agent;
(b) a platinum-based chemotherapeutic agent comprising a platinum (IV) co-ordination complex;
(c) a platinum-based chemotherapeutic agent represented by the following general structure:

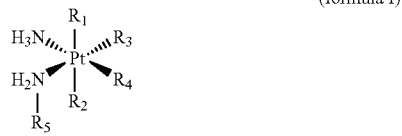

(formula I)

wherein $R_1$ and $R_2$ may be present or absent, each of $R_1$-$R_4$ is independently selected from halogen, hydroxyl, and acetate, and $R_5$ is a cycloalkyl;
(d) satraplatin or a metabolite of satraplatin;
or a pharmaceutically acceptable salt, isomer or prodrug of (a) to (d), in the treatment of a cancer or a tumor. In particular embodiments said inhibitor of a receptor of the EGFR family is herceptin or erlotinib and/or said subject platinum-based chemotherapeutic agent is satraplatin or JM118. In other embodiments said chemotherapeutically active pyrimidine analogue is gemcitabine, capecitabine or 5FU and/or said subject platinum-based chemotherapeutic agent is satraplatin or JM118.

Several embodiments of the present invention provide for the sequential administration of the compounds, or the sequential contact or sequential exposure of a tumor, a cancer or a cell derived from or comprised in a tumor or a cancer, with the compounds of the present invention. For example, the pharmaceutical packages and the uses described herein provide for such sequential administration. Also, a tumor, a cancer or a cell derived from or being part of a tumor or a cancer may be brought in contact with, may be exposed to or may be treated via administration with an inhibitor of a receptor of the EGFR family or a chemotherapeutically active pyrimidine analogue at least 1 day, 2 days, 3 days, 5 days, 7 days, 10 days, or 14 days before a platinum-based chemotherapeutic agent is brought into contact with, is exposed to or is administered to said tumor, cancer or cell derived from or comprised in a tumor or a cancer. Likewise, a tumor, a cancer or a cell derived from or being part of a tumor or a cancer may be brought in contact with, may be exposed to or may be treated via administration with a platinum-based chemotherapeutic agent at least 1 day, 2 days, 3 days, 5 days, 7 days, 10 days, or 14 days before an inhibitor of a receptor of the EGFR family or a chemotherapeutically active pyrimidine analogue is brought into contact with, is exposed to or is administered to said tumor, cancer or cell derived from or comprised in a tumor or a cancer.

The present invention also provides a kit for administering a first and a second pharmaceutical composition to an individual suffering from a cancer or a tumor, wherein said kit includes a plurality of separate containers, the contents of at least two containers differing from each other in whole or in part, wherein at least one of such containers contains an inhibitor of a receptor of the EGFR family or a chemotherapeutically active pyrimidine analogue, with or without additional pharmaceutical carrier or diluent, and at least one different container contains a subject platinum-based chemotherapeutic agent selected from:
(a) an orally available platinum-based chemotherapeutic agent;
(b) a platinum-based chemotherapeutic agent comprising a platinum (IV) co-ordination complex;
(c) a platinum-based chemotherapeutic agent represented by the following general structure:

(formula I)

wherein $R_1$ and $R_2$ may be present or absent, each of $R_1$-$R_4$ is independently selected from halogen, hydroxyl, and acetate, and $R_5$ is a cycloalkyl;
(d) satraplatin or a metabolite of satraplatin;
or a pharmaceutically acceptable salt, isomer or prodrug of (a) to (d),
with or without additional pharmaceutical carrier or diluent. In more specific aspects said platinum-based chemotherapeutic agent is, or on administration results in, a compound of formula II.

In certain embodiments, the container of the kit containing an inhibitor of a receptor of the EGFR family or a chemotherapeutically active pyrimidine analogue does not contain a subject platinum-based chemotherapeutic agent, and/or the container of the kit containing a subject platinum-based chemotherapeutic agent does not contain an inhibitor of a receptor of the EGFR family or a chemotherapeutically active pyrimidine analogue.

In yet other embodiments, the container of the above kit containing an inhibitor of a receptor of the EGFR family or a chemotherapeutically active pyrimidine analogue and the container of the above kit containing a subject platinum-based chemotherapeutic agent are amongst, or represent, the at least two containers differing from each other in respect of their content in whole or in part.

In certain embodiments the kit further comprises instructions to administer, to an individual suffering from a cancer or a tumor, a first pharmaceutical composition containing an inhibitor of a receptor of the EGFR family or a chemotherapeutically active pyrimidine analogue and a second pharmaceutical composition containing a subject-platinum-based chemotherapeutic agent within about 14 days of each other. In particular embodiments said inhibitor of a receptor of the EGFR family is herceptin or erlotinib and/or said subject platinum-based chemotherapeutic agent is satraplatin or JM118. In other embodiments said chemotherapeutically active pyrimidine analogue is gemcitabine, capecitabine or 5FU and/or said subject platinum-based chemotherapeutic agent is satraplatin or JM118. In certain embodiments said first and said second pharmaceutical composition are administered within 1 day, 2 days, 3 days, 5 days, 7 days, 10 days or 14 days of each other.

The present invention also provides for a packaged pharmaceutical, first pharmaceutical composition, use or kit as defined above, wherein said administration:
(i) is the sequential administration to said individual of an inhibitor of a receptor of the EGFR family or a chemotherapeutically active pyrimidine analogue as defined above and a subject platinum-based chemotherapeutic agent as defined above within about 14 days of each other; or
(ii) results in the sequential contact of a cell included in, derived from or being part of said cancer or tumour with an inhibitor of a receptor of the EGFR family or a chemotherapeutically active pyrimidine analogue as defined above and a subject platinum-based chemotherapeutic agent as defined above within about 14 days of each other.

Furthermore, the present invention also provides for a packaged pharmaceutical, first pharmaceutical composition, use or kit as defined above, wherein said administration:
(i) is the sequential administration to said individual of first an inhibitor of a receptor of the EGFR family or a chemotherapeutically active pyrimidine analogue as defined above and then a subject platinum-based chemotherapeutic agent as defined above within about 14 days of each other;
(ii) results in the sequential contact of a cell included in, derived from or being part of said cancer or tumor with first an inhibitor of a receptor of the EGFR family or a chemotherapeutically active pyrimidine analogue as defined above and then a subject platinum-based chemotherapeutic agent as defined above within about 14 days of each other;
(iii) is the sequential administration to said individual of first a subject platinum-based chemotherapeutic agent as defined above and then an inhibitor of a receptor of the EGFR family or a chemotherapeutically active pyrimidine analogue as defined above within about 14 days of each other; or
(iv) results in the sequential contact of a cell included in, derived from or being part of said cancer or tumor with first a subject platinum-based chemotherapeutic agent as defined above and then an inhibitor of a receptor of the EGFR family or a chemotherapeutically active pyrimidine analogue as defined above within about 14 days of each other.

In particular embodiments said inhibitor of a receptor of the EGFR family is herceptin or erlotinib and/or said subject platinum-based chemotherapeutic agent is satraplatin or JM118. In other embodiments said chemotherapeutically active pyrimidine analogue is gemcitabine, capecitabine or 5FU and/or said subject platinum-based chemotherapeutic agent is satraplatin or JM118.

The present invention also provides for a packaged pharmaceutical, first pharmaceutical composition, use or kit as defined above, wherein said administration:
(i) is the sequential administration to said individual of an inhibitor of a receptor of the EGFR family or a chemotherapeutically active pyrimidine analogue as defined above and a subject platinum-based chemotherapeutic agent as defined above within about 10 days, 7 days, 5 days, 3 days, 2 days or 1 day of each other; or
(ii) results in the sequential contact of a cell included in, derived from or being part of said cancer or tumour with an inhibitor of a receptor of the EGFR family or a chemotherapeutically active pyrimidine analogue as defined above and a subject platinum-based chemotherapeutic agent as defined above within about 10 days, 7 days, 5 days, 3 days, 2 days or 1 day of each other.

The present invention also provides for a packaged pharmaceutical, first pharmaceutical composition, use or kit as defined above, wherein said administration:
(i) is the sequential administration to said individual of an inhibitor of a receptor of the EGFR family or a chemotherapeutically active pyrimidine analogue as defined above and a subject platinum-based chemotherapeutic agent as defined above within about 48 hours, 24 hours, 12 hours, 8 hours, 6 hours, 4 hours, 2 hours, 1 hour, 30 mins, 15 mins or 5 mins of each other; or
(ii) results in the sequential contact of a cell included in, derived from or being part of said cancer or tumour with an inhibitor of a receptor of the EGFR family or a chemotherapeutically active pyrimidine analogue as defined above and a subject platinum-based chemotherapeutic agent as defined above within about 48 hours, 24 hours, 12 hours, 8 hours, 6 hours, 4 hours, 2 hours, 1 hour, 30 mins, 15 mins or 5 mins of each other.

In certain embodiments the first and second pharmaceutical compositions are administered to said individual effectively at the same time. In particular embodiments said inhibitor of a receptor of the EGFR family is herceptin or erlotinib and/or said subject platinum-based chemotherapeutic agent is satraplatin or JM118. In other embodiments said chemotherapeutically active pyrimidine analogue is gemcitabine, capecitabine or 5FU and/or said subject platinum-based chemotherapeutic agent is satraplatin or JM118.

In some embodiments of this invention said platinum-based chemotherapeutic agent is administered orally. In particular embodiments said platinum-based chemotherapeutic agent is satraplatin or JM118. In some embodiments of this invention said inhibitor of a receptor of the EGFR family or said chemotherapeutically active pyrimidine analogue is administered intravenously. In particular embodiments said inhibitor of a receptor of the EGFR family is herceptin or erlotinib. In other embodiments said chemotherapeutically active pyrimidine analogue is gemcitabine, capecitabine or 5FU. Most preferably, satraplatin or JM118 is administered orally and herceptin or erlotinib is administered intravenously. Alternatively, satraplatin or JM118 is administered orally and gemcitabine, capecitabine or 5FU is administered intravenously. These preferred routes of administration pertain to all methods, uses, pharmaceutical packages and other aspects of the present invention.

In further embodiments, the present invention provides a packaged pharmaceutical comprising a first pharmaceutical composition and instructions to administer, to an individual suffering from a cancer or a tumor, said first pharmaceutical composition and a second pharmaceutical composition, wherein:

(i) the first or second pharmaceutical composition contains an inhibitor of a receptor of the EGFR family or a chemotherapeutically active pyrimidine analogue as defined above;

(ii) the other pharmaceutical composition is a subject platinum-based chemotherapeutic agent as defined above; and (iii) said administration results in sequential contact of said subject platinum-based chemotherapeutic agent and said inhibitor of a receptor of the EGFR family or said chemotherapeutically active pyrimidine analogue with a cell included in, derived from or being part of the cancer or tumor of said individual, within 14 days of each other. In particular embodiments said inhibitor of a receptor of the EGFR family is herceptin or erlotinib and/or said subject platinum-based chemotherapeutic agent is satraplatin or JM118. In other embodiments said chemotherapeutically active pyrimidine analogue is gemcitabine, capecitabine or 5FU and/or said subject platinum-based chemotherapeutic agent is satraplatin or JM118.

The EGFRi or PA/subject platinum-based compound combination can be formulated and administered to treat individuals with cancer by any means that produces contact of the active ingredients with the agent's site of action in the body of a mammal. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In particular embodiments, the administration of said pharmaceutical formulations leads to a situation, in which the subject platinum-based compound is in contact with the agent's site of action in the body of an individual, before the inhibitor of a receptor of the EGFR family or the chemotherapeutically active pyrimidine analogue is in contact with the agent's site of action in the body of an individual. In other particular embodiments the administration of said pharmaceutical formulations leads to a situation, in which the inhibitor of a receptor of the EGFR family or the chemotherapeutically active pyrimidine analogue is in contact with the agent's site of action in the body of an individual, before the platinum-based compound is in contact with the agent's site of action in the body of an individual.

Pharmaceutical compositions for use in accordance with the present invention may be formulated in conventional manner using one or more physiologically acceptable carriers or excipients. The pharmaceutical compositions of the invention can be formulated for a variety of routes of administration, including systemic and topical or localized administration. Techniques and formulations generally may be found in Remington's Pharmaceutical Sciences, Meade Publishing Co., Easton, Pa. For systemic administration, injection is preferred, including intramuscular, intravenous, intraperitoneal, and subcutaneous (i.m., i.v., i.p., and s.c. respectively). For injection, the pharmaceutical compositions of the invention can be formulated in liquid solutions, preferably in physiologically compatible buffers such as Hank's solution or Ringer's solution. In addition, the pharmaceutical compositions may be formulated in solid form and redissolved or suspended immediately prior to use. Lyophilized forms are also included.

The term "preparation of a [first] pharmaceutical composition", refers to any process or method performed or required in the generation of a [first] pharmaceutical composition which is ready to be administered to a patient or an individual in need thereof. This includes the manufacture of the pharmaceutical composition, the formulation of the pharmaceutical composition, packaging of the pharmaceutical composition, and other steps performed before the pharmaceutical composition is delivered, requested or made available to a pharmacist, doctor or nurse. It also includes methods and processes performed by the pharmacist, doctor or nurse prior to the administration of the pharmaceutical composition. This includes, for example, dissolving the pharmaceutical composition in an appropriate solvent for administration, e.g. injection, and other steps performed by such a person which aids, facilitates, makes possible or enables the administration of the pharmaceutical composition.

The most preferred administration route of the subject platinum-based composition is oral. In oral administration, the pharmaceutical compositions may take the form of, for example, unit dose-forms such as tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active agent. In certain embodiments such a controlled release of the active agent is preferred. In certain embodiments the controlled release leads to a situation, in which the subject platinum-based compound is in contact with the agent's site of action in the body of an individual, before the inhibitor of a receptor of the EGFR family or the chemotherapeutically active pyrimidine analogue is in contact with the agent's site of action in the body of an individual. In other embodiments the controlled release leads to a situation, in which the inhibitor of a receptor of the EGFR family or the chemotherapeutically active pyrimidine analogue is in contact with the agent's site of action in the body of an individual, before the subject platinum-based compound is in contact with the agent's site of action in the body of an individual. For buccal administration the therapeutic compositions may take the form of tablets or lozenges formulated in a conventional manner. For administration by inhalation, the compositions for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, for example, gelatine for use in an inhaler or insufflator may be formulated containing a powder mix of the therapeutic agents and a suitable powder base such as lactose or starch.

The pharmaceutical compositions may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The pharmaceutical compositions may also be formulated as a depot preparation. In some embodiment it is preferred that such a formulation leads to a situation, in which the subject platinum-based compound is in contact with the agent's site of action in the body of an individual, before the inhibitor of a receptor of the EGFR family or the chemotherapeutically active pyrimidine analogue is in contact with the agent's site of action in the body of an individual. In other embodiment it is preferred that such a formulation leads to a situation, in which the inhibitor of a receptor of the EGFR family or the chemotherapeutically active pyrimidine analogue is in contact with the agent's site of action in the body of an individual, before the subject platinum-based compound is in contact with the agent's site of action in the body of an individual. Such long acting formulations may be administered by implantation (for example subcutaneously or intramuscularly) or by intramuscular injection. Thus, for example, the therapeutic compositions may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the compositions of the invention are formulated into ointments, salves, gels, or creams as generally known in the art. A wash solution can be used locally to treat an injury or inflammation to accelerate healing. For oral administration, the therapeutic compositions are formulated into conventional oral administration forms such as capsules, tablets, and tonics.

The pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. In other embodiments, the pack or dispenser may be further packaged in an outer carton. The pack or dispenser device may further comprise instructions to first administer one of the compounds of the EGFRi or PA/subject platinum-based compound combination. In some embodiments said first compound to administer is an inhibitor of a receptor of the EGFR family or a chemotherapeutically active pyrimidine analogue. In other embodiments said first compound to administer is a subject platinum-based compound.

In certain particular embodiments the EGFRi or PA/subject platinum-based compound combination is formulated as a sustained and/or timed release formulation. Such sustained and/or timed release formulations may be made by sustained release means or delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556; and 5,733,566, the disclosures of which are each incorporated herein by reference. The pharmaceutical compositions of the present invention can be used to provide slow or sustained release of one or more of the active ingredients. In certain embodiments the slow or sustained release of one or more of the active ingredients leads to a situation, in which the subject platinum-based compound is in contact with the agent's site of action in the body of an individual, before the inhibitor of a receptor of the EGFR family or the chemotherapeutically active pyrimidine analogue is in contact with the agent's site of action in the body of an individual. In other embodiments the slow or sustained release of one or more of the active ingredients leads to a situation, in which the inhibitor of a receptor of the EGFR family or the chemotherapeutically active pyrimidine analogue is in contact with the agent's site of action in the body of an individual, before the subject platinum-based compound is in contact with the agent's site of action in the body of an individual. In order to provide the desired release profile in varying proportions, hydroxypropylmethyl cellulose, other polymer matrices, gels, permeable membranes, osmotic systems, multilayer coatings, microparticles, liposomes, microspheres, or the like, or a combination thereof can be used. Suitable sustained release formulations known to those of ordinary skill in the art, including those described herein, may be readily selected for use with the pharmaceutical compositions of the invention. Thus, single unit dosage forms suitable for oral administration, such as, but not limited to, tablets, capsules, gelcaps, caplets, powders, and the like, that are adapted for sustained release are encompassed by the present invention.

The pharmaceutical compositions of the present invention may be formulated in a neutral or salt form. Pharmaceutical-acceptable salts include the acid addition salts and are formed with inorganic acids such as, for example, hydrochloric or phosphoric acids, or such organic acids as acetic, oxalic, tartaric, mandelic, and the like. Salts formed with the free carboxy groups can also be derived from inorganic bases such as, for example, sodium, potassium, ammonium, calcium, or ferric hydroxides, and such organic bases as isopropylamine, trimethylamine, histidine, procaine and the like.

The EGFRi or PA/subject platinum-based compound combination can also be co-administered with a variety of other drugs. For example, the EGFRi or PA/subject platinum-based compound combination can be used as part of a regiment of treatment in which it is combined with other chemotherapeutic agents including anti-cancer therapeutic agents that inhibit cancer growth, anti-angiogenesis agents and anti-metastatic agents. The subject pharmaceutical compositions may also be combined with immunomodulators. One compound which may be administered with the EGFRi or PA/subject platinum-based compound combination is prednisone. Prednisone is a corticosteroid prodrug that is converted into the active drug prednisolone in the liver.

In a further embodiment, the EGFRi or PA/subject platinum-based compound combination is administered to a patient to whom an anti-emetic agent is also administered. Anti-emetic agents according to this invention include any anti-emetic agents known to the skill artisan, including, but not limited to, serotonin-3 receptor antagonists like granisetron, ondansetron and tropisetron, NK1 receptor antagonists, antihistamines such as cinnarizine, cyclizine and promethazine, histamine H2 receptor antagonists such as ranitidine (Zantac), phenothiazines such as chlorpromazine, droperidol, haloperidol, methotrimeprazine, perphenazine, trifluoperazine and prochlorperazine, domperidone, and metoclopramide.

In other embodiments, the EGFRi or PA/subject platinum-based compound combination is administered to a patient who is also treated with an anti-diarrheal such as loperamid, corticosteroid such as cortisone, growth hormone or growth factor such as GCSF or erythropoietin, a diuretica such as furosemid, steroidal or non-steroidal analgesics such as an opiate, e.g. morphine, or paracetamol or anti-hyperuricemics such as allopurinol.

In other embodiments, the EGFRi or PA/subject platinum-based compound combination is administered to a patient, who is also treated with thrombocytes, erythrocytes or whole blood.

In other embodiments, the EGFRi or PA/subject platinum-based compound combination is administered to a patient, who is also treated with stem cells of the bone marrow.

In other embodiments, the instant invention also relate to a method of therapeutic patient care. In the method, a patient who is treated via administration with the EGFRi or PA/subject platinum-based compound combination receives food parenterally.

The present invention additionally provides methods for preparing a pharmaceutical composition useful for the treatment of an individual suffering from a cancer or tumor. The methods comprise:
 a) compiling data including:
  i. bioequivalence data for a compound combination comprising an inhibitor of a receptor of the EGFR family or a chemotherapeutically active pyrimidine analogue as defined above and a subject platinum-based chemotherapeutic agent as defined above, or a pharmaceutically acceptable salt, isomer or prodrug thereof, compared to a marketed originator compound or compound combination; or
  ii. clinical data demonstrating the effectiveness of said EGFRi or PA/subject platinum-based compound combination in treating cancer patients;
 b) submitting said compiled data to a drug regulatory authority for the purpose or obtaining regulatory or marketing approval for said EGFRi or PA/subject platinum-based compound combination for the treatment of cancer patients; and
 c) manufacturing, importing, packaging/re-packaging, labeling/re-labeling or marketing said EGFRi or PA/subject platinum-based compound combination, or license rights to said approval, for the treatment of cancer patients.

The dosage administered will be a therapeutically effective amount of the EGFRi or PA/subject platinum-based compound combination sufficient to result in, or reasonable expected to result in, amelioration of symptoms of the cancer or tumor and will, of course, vary depending upon known factors such as the pharmacodynamic characteristics of the particular active ingredient and its mode and route of administration; age, sex, health and weight of the recipient; nature and extent of symptoms; kind of concurrent treatment, frequency of treatment and the effect desired.

Toxicity and therapeutic efficacy of pharmaceutical compositions of the present invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapeutic agents which exhibit large therapeutic indices are preferred. While therapeutic compositions that exhibit toxic side effects may be used, care should be taken to design a delivery system that targets such therapeutic agents to the site of affected tissue in order to minimize potential damage to uninfected cells and, thereby, reduce side effects.

The data obtained from cell culture assays and animal studies can be used in formulating a range of dosage for use in humans. The dosage lies preferably within a range of circulating concentrations that include the ED50 with little or no toxicity. The dosage may vary within this range depending upon the dosage form employed and the route of administration utilized. For any agents used in the various aspects of the invention, the therapeutically effective dose can be estimated initially from cell culture assays. A dose may be formulated in animal models to achieve a circulating plasma concentration range that includes the IC50 (i.e., the concentration of the test therapeutic agent which achieves a half-maximal inhibition of symptoms or inhibition of biochemical activity) as determined in cell culture. Such information can be used to more accurately determine useful doses in humans. Levels in plasma may be measured, for example, by high performance liquid chromatography.

It is understood that appropriate doses of therapeutic agents depends upon a number of factors known to those or ordinary skill in the art, e.g., a physician. The dose(s) of the small molecule will vary, for example, depending upon the identity, size, and condition of the subject or sample being treated, further depending upon the route by which the composition is to be administered, if applicable, and the effect which the practitioner desires the therapeutic to have upon the therapeutic target of targets, such as nucleic acid or polypeptide of the invention, through with the disease causes, symptoms or effects are mediated. As will be self-evident, for combination therapy the combined effect of both compounds, the inhibitor of a receptor of the EGFR family or a chemotherapeutically active pyrimidine analogue and the subject platinum-based compound, will have to be taken into account.

Exemplary doses include milligram or microgram amounts of the small molecule(s), i.e. the inhibitor of a receptor of the EGFR family or a chemotherapeutically active pyrimidine analogue and the subject platinum-based chemotherapeutic agent, per kilogram of subject or sample weight, e.g., about 1 microgram per kilogram to about 500 milligrams per kilogram, about 100 micrograms per kilogram to about 50 milligrams per kilogram, or about 1 milligram per kilogram to about 5 milligrams per kilogram.

A person skilled in the art will appreciate that doses can also be calculated on a body surface basis. A person of 70 kg has an approximate body surface area of 1.8 square meter doses include milligram or microgram amounts of the small molecule per body surface area of subject or sample, e.g. about 50 microgram per square meter to about 15 grams per square meter, about 5 milligrams per square meter to about 1.5 grams per square meter, or about 50 milligram per square meter to about 150 milligrams per square meter.

8. Treatment of Resistant or Refractory Cancers and Tumors

Cancers or tumors that are resistant or refractory to treatment of a variety of anti-proliferative agents may benefit from treatment with the methods of the present invention. In certain alternative embodiments of the instant invention, the EGFRi or PA/subject platinum-based compound combination may be useful in treating tumors that are refractory or resistant to an anti-proliferative agent. In particular embodiments said anti-proliferative agent is not a hormone-based drug. In other particular embodiments said anti-proliferative agent is cisplatin. Resistance to anti-proliferative agents can be tested and verified using the methods described in the Examples.

As used herein, the term "anti-proliferative agent" relates to any compound which is or may be used in the treatment of a "proliferative disorder", as defined herein. Exemplary anti-proliferative agents include vinca alkaloids (vinblastine), the anthracyclines (adriamycin), the epipodophyllotoxins (etoposide), antibiotics (actinomycin D and gramicidin D), anti-microtubule drugs (colchicine), protein synthesis inhibitors (puromycin), toxic peptides (valinomycin), topoisomerase I inhibitors (topotecan), DNA intercalators (ethidium bromide), anti-mitotics, vinca alkaloids (vinblastine, vincristine, vindesine and vinorelbine), epothilones (epothilone A, epothilone B and discodermolide), nocodazole, colchicine, colchicine derivatives, allocolchicine, Halichondrin B, dolstatin 10, maytansine, rhizoxin, thiocolchicine, trityl cysterin, estramustine, nocodazole, platinum-based agents (cisplatin, paraplatin, carboplatin, but not the subject platinum-based chemotherapeutic agents as defined herein), camptothecin, 9-nitrocamptothecin (Orethecin, rubitecan), 9-aminocamptothecin (IDEC-13'), exatecan (DX-8951f), lurtotecan (GI-147211C), BAY 38-3441, the homocamptothecins such as diflomotecan (BN-80915) and BN-80927, topotecan (Hycamptin), NB-506, J107088, pyrazolo[1,5-a]indole derivatives, such as GS-5, Iamellarin D, irinotecan (Camptosar, CPT-11), and antibodies, such as 1D10, Hu1D10, 1D09C3, 1C7277, 305D3, rituximab, 4D5, Mab225, C225, Daclizumab (Zenapax), Antegren, CDP 870, CMB-401, MDX-33, MDX-220, MDX-477, CEA-CIDE, AHM, Vitaxin, 3622W94, Therex, 5G1.1, IDEC-131, HU-901, Mylotarg, Zamyl (SMART M195), MDX-210, Humicade, Lympho-CIDE, ABX-EGF, 17-1A, Epratuzumab, Cetuximab (Erbitux®), Pertuzumab (Omnitarg®, 2C4), R3, CDP860, Bevacizumab (Avastin®), tositumomab (Bexxar®), Ibritumomab tiuxetan (Zevalin®), M195, 1D10, Hu1D10 (Remitogen®, apolizumab), Danton/DN1924, an "HD" antibody such as HD4 or HD8, CAMPATH-1 and CAMPATH-1H or other variants, fragments, conjugates, derivatives and modifications thereof, or other equivalent compositions with improved or optimized properties.

Refractory cancers or tumors include those that fail or are resistant to treatment with anti-proliferative agents alone, radiation alone or combinations thereof. For the purposes of this specification, refractory cancers or tumors also encompass those that appear to be inhibited by treatment with chemotherapeutic agents and/or radiation but recur up to five years, sometimes up to ten years or longer after treatment is discontinued.

The term "resistant", as used herein, include both partially resistant and completely resistant. Thus, a tumor that is only partially resistant to an anti-proliferative agent may nonetheless benefit from treatment with the EGFRi or PA/subject platinum-based compound combination. Indeed, in certain embodiments it may be beneficial to treat a tumor if such resistance is merely suspected, may not yet be know or even before such resistance has developed. In alternative embodiments, it may be subsequently determined, or not at all, that the cancer or tumor was resistant or refractory to an anti-proliferative agent.

In particular embodiments said anti-proliferative agent is not a hormone-based drug. In certain embodiments said anti-proliferative agent is not a pituitary down-regulator. In other embodiments said anti-proliferative agent is not an anti-androgen.

The term "hormone-based drug" refers to compounds which are used in hormonal treatment. Such compounds may be hormones or derivatives or variants of hormones. Hormone-based drugs also include molecules which are neither hormones, nor derivatives or variants of hormones, yet affect the production or action of hormones. Treatment with hormone-based drugs is referred to as "hormone ablation therapy". Hormone ablation therapy aims at limiting the growth of a cancer or tumor by limiting the supply of hormones that this type of cancer or tumor needs for growth.

Some types of cancer, e.g. cancer of the prostate, depend on hormones, e.g. testosterone, for growth. If the amount of testosterone is reduced it is often possible to slow down or shrink the tumour. Such treatment is usually effective for a limited time, typically for 18 to 24 months. After that, the tumor may stop responding to the treatment and resume growth, i.e. hormone refractory prostate cancer (HRPC) develops.

Testosterone levels can be reduced, for example, by surgery (e.g. removel of the testes) or by drug-based treatment, including hormone-based drug treatment. There are two main types of such hormone based drugs. First, pituitary down-regulators block luteinizing hormone-releasing hormone (LHRH), which is released by the pituitary gland. LHRH, if not blocked is a stimulus for the testes to produce testosterone. Examples of such pituitary down-regulators include leuprorelin (Prostap), triptorelin (De-capaptyl), buserelin (Suprefact) and goserelin (Zoladex). Second, anti-androgens block the action of testosterone at the prostate. Examples of such anti-androgens include cyproterone acetate (Cyprostat), flutamide (Eulexin, Drogenil), nilutamide (Nilandrone) and bicalutamide (Casodex). It will be appreciated that other types of cancer may also be treated with hormone-based drugs. These include, but is not limited to, breast cancer, uterine cancer, thyroid cancer and colon cancer.

The practice of aspects of the present invention may employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); *Manipulating the Mouse Embryo*, (Cold Spring Harbor Laboratory Press, Cold Spring Harbor, N.Y., 1986). All patents, patent applications and references cited herein are incorporated in their entirety by reference.

While the invention has been described and exemplified in sufficient detail for those skilled in this art to make and use it, various alternatives, modifications, and improvements should be apparent without departing from the spirit and scope of the invention.

Those skilled in the art will recognize, or be able to ascertain using no more than routine experimentation, many equivalents to the specific embodiments of the invention described herein. Such equivalents are intended to be encompassed by the following claims. Those skilled in the art will also recognize that all combinations of embodiments or features of the embodiments described herein are within the scope of the invention.

EXEMPLIFICATION

Example 1

Efficacy of Satraplatin and its Metabolites is Maintained in Cisplatin-resistant Tumor Cells We observed the surprising finding that subject platinum-based compounds of the invention were useful in inhibiting or killing tumour cells that were resistant to other platinum compounds, such as cisplatin.

The A129 cp80 cell line (received from Tito Fojo, NIH; Biochem Pharmacol (1996) 52, 1855), derived from the ovarian carcinoma A2780, was highly resistant to cisplatin—relative resistance in individual experiments ranged between 8° to 106-fold—yet remained susceptible to treatment with JM216, JM118 and JM383—relative resistance in individual experiments between 0.19 to 2.59-fold (Table 1). The parental non-mutated cell line A129 was used as control.

1,000-5,000 cells/well were contacted with the test compounds for 48 hours at various concentrations in order to calculate the IC50 values shown in Table 1. Cytotoxicity was measured using the SRB assay according to Shekan et al. (J Natl Cancer Inst (1990) 82, 1107-112). Briefly, cells were plated in 96 well dishes 24 hours prior to compound addition. The assay was terminated with the addition of cold TCA to a final concentration of 10% and the plates were incubated for one hour at 4° C. The plates were then washed 5 times with water and 100 µl of a Sulforhodamine B solution (4%) was added to each well. The plate was then incubated for 10 minutes at room temperature before removal of unbound dye by washing with 1% acetic acid. The bound dye was solubilized with 10 mM Trizma base and the absorbance read at OD570.

TABLE 1

Cellular IC50's of Satraplatin and metabolites in Cisplatin resistant cells

| Compound | Cell line A129 IC50 (µM) | A129 cp80 IC50 (µM) | RR |
| --- | --- | --- | --- |
| Cisplatin | 0.23 +/− 0.17 (3) | 15.1 +/− 6.4 (3) | 80 +/− 25 |
| Satraplatin (JM216) | 0.30 +/− 0.24 (3) | 1.54 +/− 0.72 (3) | 5.9 +/− 1.9 |
| JM118 | 0.24 +/− 0.14 (3) | 0.69 +/− 0.52 (3) | 2.6 +/− 0.9 |
| JM383 | 1.29 +/− 0.11 (2) | 1.78 +/− 1.15 (2) | 1.4 +/− 1.0 |

Legend:
Table 1 shows the IC50 values as determined in the experiments described in Example 1. Numbers in brackets indicate how often experiments were performed. In each single experiment a minimum of three replica wells was used for each drug concentration and cell line. Shown are mean values and standard deviations of the IC50s, as determined in the individual experiments. RR denominates the relative resistance, i.e. the relative level of resistance conferred to the indicated drugs.

Example 2

Synergism Between the Subject Platinum-based Compounds and Inhibitors of Receptors of the EGFR Family We demonstrate the surprising finding that various inhibitors of receptors of the EGFR family act synergistically with the subject platinum-based compounds. This is shown with herceptin (trastuzumab), a monoclonal antibody which binds to ErbB2 (Her2, EGFR2; see Example 2.1) and with erlotinib (Tarceva), a small molecule inhibitor of ErbB1 (EGFR1, Her1; Example 2.2).

Example 2.1

Synergism Between the Subject Platinum-based Compounds and Herceptin (Trastuzumab)

We observed the surprising finding that JM-118 acts synergistically in combination with herceptin when exposed to or brought into contact with cancer cells.

The cell line used was the human breast adenocarcinoma cell line SKBR-3 (ATCC order number: HTB-30; Recent Results Cancer Res (1976) 57, 33; J Natl Cancer Inst (1977) 59, 221). RPMI with 10% FCS, 1% L-glutamine and 100 U/ml penicillin/100 µg/ml streptomycin was used as growth medium and cells were maintained at 37° C. and 5% $CO_2$.

JM-118 was dissolved in saline at a concentration of 0.5 mM and herceptin was dissolved in water at a concentration of 0.25 mM.

Cells were seeded in 96 well plates at a density of 2,000 cells per well for twenty-four hours. For simultaneous combination treatment cells were then contacted with different concentrations of JM-118, herceptin or a combination of JM-118 and herceptin. Control wells were contacted with the respective solvents (saline for JM-118, water for herceptin). Cells were incubated for 96 hours at 37° C. and 5% $CO_2$. For sequential combination treatments cells were first incubated for 120 hours with herceptin, followed by 24 hours incubation with JM-118. After treatment with the first compound cells were washed three times with prewarmed PBS/10% FCS, before the cells were incubated further with the second compound. Control treatments for the sequential combination studies were performed in the same manner, but the second compound treatment was replaced by incubation with the solvent. For both treatment schedules, simultaneous combination treatment and sequential combination treatments, cytotoxicity was measured using the SRB assay according to Shekan et al. (Example 1; J Natl Cancer Inst (1990) 82, 1107-112).

The combination index (CI; Adv Enzyme Regul (1984) 22,27) was calculated with the algorithm of Chou using XLfit 4.1 (IDBS Ltd., Guildford, UK). CI values of <1, ≈1 and >1 indicate synergism, additive effect and antagonism, respectively. FIG. 2 shows the isobologram. The combination of JM-118 and herceptin showed a clear and strong synergistic effect for both treatment schedules. The isobologram shows the data points for all drug combinations, but is calculated only for 50% growth inhibition.

Synergy was also evaluated by calculation of the Bliss Independece (Ann Appl Biol (1939) 26, 585). Results are summarized in Tables 2 and 3.

TABLE 2

Simultaneous combination treatment of the SKBR-3 cell line with JM-118 and herceptin

| Growth inhibition | | Herceptin (μM) | | | | |
|---|---|---|---|---|---|---|
| | | 0 | 0.0020 | 0.0039 | 0.0078 | 0.0156 | 0.0313 |
| JM118 (μM) | 0 | 0.0% | 41.4% | 44.7% | 48.0% | 51.4% | 54.8% |
| | 0.09375 | 8.3% | 56.5% (s) | 57.0% (s) | 61.2% (s) | 56.5% (s) | 62.1% (s) |
| | 0.1875 | 21.7% | 69.6% (s) | 70.6% (s) | 65.1% (s) | 71.8% (s) | 75.0% (s) |
| | 0.375 | 46.8% | 79.9% (s) | 83.2% (s) | 86.9% (s) | 89.9% (s) | 88.3% (s) |
| | 0.75 | 76.3% | 91.6% (s) | 95.2% (s) | 95.4% (s) | 98.2% (s) | 98.6% (s) |
| | 1.5 | 96.6% | 95.8% (n) | 97.7% (n) | 99.5% (s) | 96.8% (n) | 100.0% (s) |

Legend:

Table 2 shows the effect of the combination treatment with herceptin and JM-118 on the SKBR-3 cell line. Cells were incubated with both compounds simultaneously. Bliss independence was used to calculate whether an individual combination of the two compounds elicited a synergistic effect. '(s)' indicates that the individual combination showed a synergistic effect. '(n)' denotes that the respective combination did not act synergistically according to Bliss independence.

TABLE 3

Sequential combination treatment of the SKBR-3 cell line with herceptin for 120 hours, followed by JM-118 for 24 hours

| Growth inhibition | | Herceptin (μM) | | | | | |
|---|---|---|---|---|---|---|---|
| | | 0 | 0.0020 | 0.0039 | 0.0078 | 0.0156 | 0.0313 |
| JM118 (μM) | 0 | 0.0% | 28.1% | 30.9% | 34.1% | 37.4% | 41.1% |
| | 0.078125 | 13.1% | 47.5% (s) | 57.6% (s) | 56.4% (s) | 54.7% (s) | 56.4% (s) |
| | 0.15625 | 16.0% | 46.2% (s) | 49.5% (s) | 55.8% (s) | 52.0% (s) | 55.5% (s) |
| | 0.3125 | 19.4% | 35.0% (n) | 55.8% (s) | 60.5% (s) | 54.4% (s) | 58.3% (s) |
| | 0.625 | 23.6% | 44.2% (n) | 53.1% (s) | 56.2% (s) | 55.7% (s) | 60.1% (s) |
| | 1.25 | 28.5% | 58.3% (s) | 63.3% (s) | 70.0% (s) | 62.9% (s) | 63.8% (s) |

Legend:

Table 3 shows the effect of the combination treatment with herceptin and JM-118 on the SKBR-3 cell line. Cells were incubated with both compounds sequentially, wherein cells were incubated with herceptin first. Bliss independence was used to calculate whether an individual combination of the two compounds elicited a synergistic effect. '(s)' indicates that the individual combination showed a synergistic effect. '(n)' denotes that the respective combination did not act synergistically according to Bliss independence.

Example 2.2

Synergism Between the Subject Platinum-based Compounds and Erlotinib (Tarceva)

We also observed the surprising finding that JM-118 acts synergistically in combination with erlotinib (Tarceva) when exposed to or brought into contact with cancer cells or tumor cells sequentially. Synergism was most pronounced when the cancer cells or tumor cells were exposed to or brought into contact with the subject platinum-based compound first.

For this experiment the human non small cell lung cancer (NSCLC) cell line H460 was used (ATCC deposit number HTB-177). H460 cells were cultured in modified RPMI-1640 complete medium supplied with 10% fetal calf serum (FCS) and 1% Penicillin/Streptomycin.

Cells were seeded in 96 well dishes at a density of 3,500 cells per well for 48 hour treatments, for longer treatments cells were seeded at a density of 1,500 cells per well. Erlotinib was dissolved in 0.1% DMSO. Twenty-four hours after plating, the cells were contacted with the test compounds depending on the schedule as indicated below. Cytotoxicity was measured using the SRB assay according to Shekan et al. (Example 1; J Natl Cancer Inst (1990) 82, 1107-112).

Cells were incubated for 48 hours or 96 hours for single treatments with JM118 or erlotinib. Control treatment were performed with identical volumes of the solvent (saline for JM118; 0.1% DMSO for erlotinib). The same incubation periods of 48 hours or 96 hours was used for the simultaneous combination treatment of JM118 and erlotinib. For sequential combination treatments, the incubation period was 72 hours for erlotinib and 24 hours for JM118. After treatment with the first compound cells were washed three times with prewarmed PBS/10% FCS, before the cells were incubated further with the second compound. Control treatments for the sequential combination studies were performed in the same manner, but the second compound treatment was replaced by incubation with the solvent.

Synergy was evaluated by calculation of the Bliss independence as described in Example 2.1. No synergism was observed when the cells were treated with erlotinib and JM118 simultaneously. A synergistic effect was observed however, when the cells were exposed to JM118 and erlotinib sequentially. Synergism was more pronounced, when the cancer cells or tumor cells were exposed to or brought into contact with the subject platinum-based compound, JM118, first. Results are summarized in Tables 4 and 5.

TABLE 4

Sequential combination treatment of the H460 cell line with JM118 for 24 hours, followed by erlotinib for 72 hours

| Growth Inhibition | | Erlotinib (μM) | | | | | |
|---|---|---|---|---|---|---|---|
| | 0 | 3.125 | 6.25 | 12.5 | 25 | 50 | 100 |
| JM118 (μM) 0 | 0.0% | 25.3% | 44.8% | 63.8% | 76.2% | 82.4% | 85.1% |
| 0.025 | 0.9% | 41.6% (s) | 64.2% (s) | 76.5% (s) | 78.9% (s) | 100.5% (s) | 86.7% (s) |
| 0.05 | 2.5% | 38.5% (s) | 61.7% (s) | 73.8% (s) | 76.1% (n) | 99.8% (s) | 82.4% (n) |
| 0.1 | 7.0% | 53.9% (s) | 67.7% (s) | 76.8% (s) | 83.5% (s) | 100.4% (s) | 86.0% (n) |
| 0.2 | 18.3% | 67.0% (s) | 76.7% (s) | 82.3% (s) | 87.7% (s) | 100.6% (s) | 88.6% (s) |
| 0.4 | 40.0% | 85.6% (s) | 88.9% (s) | 89.5% (s) | 92.7% (s) | 101.2% (s) | 91.4% (s) |
| 0.8 | 66.9% | 92.7% (s) | 92.4% (s) | 93.0% (s) | 96.2% (s) | 101.4% (s) | 95.1% (s) |

Legend:

Table 4 shows the effect of the combination treatment with erlotinib and JM-118 on the H460 cell line. Cells were incubated with both compounds sequentially, wherein cells were incubated with JM118 first. Bliss independence was used to calculate whether an individual combination of the two compounds elicited a synergistic effect. '(s)' indicates that the individual combination showed a synergistic effect. '(n)' denotes that the respective combination did not act synergistically according to Bliss independence.

TABLE 5

Sequential combination treatment of the H460 cell line with erlotinib for 72 hours, followed by JM118 for 24 hours

| Growth inhibition | | Erlotinib (μM) | | | | | |
|---|---|---|---|---|---|---|---|
| | 0 | 1.5625 | 3.125 | 6.25 | 12.5 | 25 | 50 |
| JM118 (μM) 0 | 0.0% | 6.9% | 14.7% | 28.7% | 48.5% | 68.9% | 84.2% |
| 0.01875 | 1.7% | 0.1% (n) | 36.1% (s) | 35.0% (s) | 58.0% (s) | 71.5% (s) | 99.3% (s) |
| 0.0375 | 3.1% | 0.5% (n) | 23.1% (s) | 24.8% (n) | 57.5% (s) | 68.3% (n) | 98.7% (s) |
| 0.075 | 5.7% | −1.3% (n) | 27.6% (s) | 29.6% (n) | 56.4% (n) | 70.1% (n) | 96.8% (s) |
| 0.15 | 10.2% | 1.0% (n) | 26.8% (s) | 39.5% (s) | 54.1% (s) | 75.5% (s) | 95.8% (s) |
| 0.3 | 18.0% | 18.0% (n) | 31.5% (s) | 40.2% (n) | 60.1% (s) | 73.2% (n) | 95.6% (s) |
| 0.6 | 30.6% | 30.8% (n) | 48.5% (s) | 60.8% (s) | 69.0% (s) | 83.3% (s) | 94.2% (s) |

Legend:

Table 5 shows the effect of the combination treatment with erlotinib and JM-118 on the H460 cell line. Cells were incubated with both compounds sequentially, wherein cells were incubated with erlotinib first. Bliss independence was used to calculate whether an individual combination of the two compounds elicited a synergistic effect. '(s)' indicates that the individual combination showed a synergistic effect. '(n)' denotes that the respective combination did not act synergistically according to Bliss independence.

Example 3

Synergism Between the Subject Platinum-based Compounds and Chemotherapeutically Active Pyrimidine Analogues We demonstrate the surprising finding that chemotherapeutically active pyrimidine analogues act synergistically with the subject platinum-based compounds. This is shown with gemcitabine (see Example 3.1) and with 5-fluoruracil (5FU; Example 3.2).

Example 3.1

Synergism Between the Subject Platinum-based Compounds and Gemcitabine

We observed the surprising finding that JM-118 acts synergistically in combination with gemcitabine when exposed to or brought into contact with cancer cells. This synergistic effect is observed when the cell are exposed to or brought into contact with cancer cells or tumor cells sequentially, and is most pronounced when the cancer cells or tumor cells are exposed to gemcitabine first.

For this experiment the human bladder carcinoma cell line UM-UC-3 was used (ATCC order number: CRL-1749; J Urol (1986) 136, 953; Cancer Res (1997) 57,516). The experiment was performed as described in Example 2.2, with the exception that JM-118 and gemcitabine were used. Gemcitabine was dissolved in saline at a concentration of 10 mM. Cells were seeded at 1,500 cells per well. Cells were incubated for 48 hours for single treatments with JM-118 and gemcitabine, and the same incubation period of 48 hours was used for the simultaneous combination treatment of JM-118 and gemcitabine. For sequential combination treatments, the incubation period was 48 hours for both compounds. Between the two treatment periods cells were washed as described in Example 2.2. Synergy was evaluated by calculation of the Bliss independence as described in Example 2.1. Results are summarized in Tables 6 and 7.

TABLE 6

Sequential combination treatment of the UM-UC3 cell line with JM-118, followed by gemcitabin

| Growth Inhibition | | Gemcitabine (μM) | | | | | |
|---|---|---|---|---|---|---|---|
| | | 0 | 0.0020 | 0.0039 | 0.0078 | 0.0156 | 0.0313 | 0.0625 |
| JM118 (μM) | 0 | 0.0% | 2.6% | 8.7% | 23.4% | 43.9% | 57.8% | 63.3% |
| | 0.03125 | 0.7% | 29.2% (s) | 24.9% (s) | 22.4% (n) | 37.0% (n) | 66.2% (s) | 82.2% (s) |
| | 0.0625 | 2.4% | 36.8% (s) | 39.6% (s) | 36.8% (s) | 45.2% (n) | 68.7% (s) | 90.5% (s) |
| | 0.125 | 8.5% | 54.8% (s) | 42.3% (s) | 48.7% (s) | 53.1% (s) | 66.7% (s) | 88.9% (s) |
| | 0.25 | 25.6% | 59.5% (s) | 58.7% (s) | 64.5% (s) | 62.0% (s) | 72.9% (s) | 89.0% (s) |
| | 0.5 | 56.3% | 68.5% (s) | 60.1% (n) | 70.2% (s) | 64.5% (n) | 73.5% (n) | 90.6% (s) |
| | 1 | 83.4% | 72.4% (n) | 64.1% (n) | 73.0% (n) | 69.2% (n) | 73.3% (n) | 87.9% (n) |

Legend:

Table 6 shows the effect of the combination treatment with gemcitabine and JM-118 on the UM-UC3 cell line. Cells were incubated with both compounds sequentially, wherein cells were incubated with JM118 first. Bliss independence was used to calculate whether an individual combination of the two compounds elicited a synergistic effect. '(s)' indicates that the individual combination showed a synergistic effect. '(n)' denotes that the respective combination did not act synergistically according to Bliss independence.

TABLE 7

Sequential combination treatment of the UM-UC3 cell line with gemcitabine, followed by JM118

| Growth Inhibition | | Gemcitabine (μM) | | | | | |
|---|---|---|---|---|---|---|---|
| | | 0 | 0.0015625 | 0.003125 | 0.00625 | 0.0125 | 0.025 | 0.05 |
| JM118 (μM) | 0 | 0.0% | 0.2% | 1.2% | 8.3% | 41.7% | 87.8% | 102.7% |
| | 0.625 | 13.1% | 32.5% (s) | 27.9% (s) | 53.0% (s) | 62.0% (s) | 73.0% (n) | 73.7% (n) |
| | 1.25 | 26.2% | 31.2% (s) | 40.9% (s) | 52.7% (s) | 58.7% (s) | 77.5% (n) | 84.9% (n) |
| | 2.5 | 43.9% | 46.5% (s) | 53.9% (s) | 57.1% (s) | 67.5% (s) | 86.7% (s) | 86.2% (n) |
| | 5 | 60.2% | 66.3% (s) | 77.2% (s) | 75.2% (s) | 79.8% (s) | 92.9% (s) | 91.7% (n) |
| | 10 | 70.8% | 89.0% (s) | 91.0% (s) | 84.4% (s) | 93.6% (s) | 99.8% (s) | 94.7% (n) |
| | 20 | 76.1% | 88.6% (s) | 96.4% (s) | 82.8% (s) | 94.7% (s) | 100.6% (s) | 97.1% (n) |

Legend:

Table 7 shows the effect of the combination treatment with gemcitabine and JM-118 on the UM-UC3 cell line. Cells were incubated with both compounds sequentially, wherein cells were incubated with gemcitabine first. Bliss independence was used to calculate whether an individual combination of the two compounds elicited a synergistic effect. '(s)' indicates that the individual combination showed a synergistic effect. '(n)' denotes that the respective combination did not act synergistically according to Bliss independence.

For most drug combinations synergy was observed when the cells were contacted with the compounds sequentially. The effect was slightly more pronounced when the cells were first brought into contact with gemcitabine (Table 7), than when the cells were first brought into contact with JM-118 (Table 6).

Example 3.2

Synergism Between the Subject Platinum-based Compounds and 5-Fluoruracil (5FU)

We also observed the surprising finding that JM-118 acts synergistically in combination with 5-fluoruracil (5FU) when exposed to or brought into contact with cancer cells.

For this experiment the human colorectal carcinoma cell line HCT 116 (ATCC order number: CCL-247; Cancer Res (1981) 41, 1751; J Natl Cancer Inst (1982) 69, 767) and the human adenocarcinoma cell line MCF7 (ATCC order number: HTB-22; Cancer Res (1983) 43, 2831; Science (1985) 230, 943) were used.

The experiment was performed as described in Example 2.2, with the following exceptions: JM-118 and 5FU were used; cells were seeded in 96 well plates at a density of 3,500 cells per well for 48 hour treatment, for longer treatments cells were seeded at a density of 1,000 cells per well. 5FU was dissolved in 0.1% DMSO at a concentration of 20 mM.

An exemplary result for the simultaneous treatment with JM118 and 5FU for 48 hours in the cell line MCF7 is shown in Table 8. Synergy was evaluated by calculation of the Bliss independence as described in Example 2.1. Similar results were observed with the cell line HCT 116. Synergy was less pronounced for all sequential treatments.

TABLE 8

Simultaneous combination treatment of the MCF7 cell line with JM-118 and 5-FU

| Growth Inhibition | | 5FU (µM) | | | | | | |
|---|---|---|---|---|---|---|---|---|
| | | 0 | 0.3125 | 0.625 | 1.25 | 2.5 | 5 | 10 |
| JM118 (µM) | 0 | 0.0% | 1.1% | 2.9% | 7.2% | 17.3% | 37.4% | 67.7% |
| | 0.1875 | 3.5% | 4.3% (n) | 3.6% (n) | 14.4% (s) | 32.2% (s) | 55.4% (s) | 64.7% (n) |
| | 0.375 | 10.8% | 26.9% (s) | 27.2% (s) | 25.9% (s) | 46.6% (s) | 63.0% (s) | 74.5% (s) |
| | 0.75 | 28.8% | 41.6% (s) | 36.7% (s) | 43.2% (s) | 53.1% (s) | 66.5% (s) | 75.5% (n) |
| | 1.5 | 57.6% | 62.4% (s) | 68.3% (s) | 66.6% (s) | 74.5% (s) | 77.0% (s) | 83.5% (n) |
| | 3 | 82.9% | 97.3% (s) | 93.6% (s) | 97.5% (s) | 97.5% (s) | 103.2% (s) | 95.3% (s) |
| | 6 | 93.9% | 100.0% (s) | 100.0% (s) | 100.0% (s) | 100.0% (s) | 100.0% (s) | 100.0% (s) |

Legend:

Table 8 shows the effect of the simultaneous combination treatment with 5FU and JM-118 in the MCF7 cell line. Cells were incubated with both compounds simultaneously. Bliss independence was used to calculate whether an individual combination of the two compounds elicited a synergistic effect. '(s)' indicates that the individual combination showed a synergistic effect. '(n)' denotes that the respective combination did not act synergistically according to Bliss independence.

Example 4

Synergism Between the Subject Platinum-based Compounds and an Inhibitor of a Receptor of the EGFR Family or a Chemotherapeutically Active Pyrimidine Analogue in a Xenograft Model We demonstrate the surprising finding that inhibitors of a receptor of the EGFR family and chemotherapeutically active pyrimidine analogues act synergistically with the subject platinum-based compounds in xenograft models. This is shown with capecitabine (see Example 4.1) and with gemcitabine (see Example 4.2).

Example 4.1

Synergism Between the Subject Platinum-based Compounds and Capecitabine in a Xenograft Model Healthy female SWISS nu/nu mice, 6-7 weeks old, 17-22 g, were obtained from Charles River (L'Arbresle, France). Animals were acclimated for seven days in a specific-pathogen-free (SPF) animal care unit before treatment. MX-1 tumor implants were purchased and provided by Oncodesign (Dijon, France). MX-1 is a human breast carcinoma cell line. The MX-1 tumor was initiated in 1974 by surgery from a primary tumor of a 29-year-old female with no previous chemotherapy (Cancer Res (1979) 39, 2928-33). The MX-1 fragments are stored in DMSO/SVF/RPMI 1640 medium (10:10:80) in liquid nitrogen until use. Fragments were thawed at 37° C. for 5 minutes, rinsed twice in RPMI 1640 medium before subcutaneous implantation in mice.

To induce MX-1 tumors in nude mice ten female SWISS nude mice were subcutaneously implanted with thawed fragments of MX-1 tumor 24 hours after whole body irradiation with a γ-source ($Co^{60}$, INRA, Dijon, France). Mice were continuously monitored and terminated when tumors reached 700 to 1000 mm³. Tumors were then surgically excised and homogenous fresh fragments were subcutaneously implanted in the right flanks of 130 SWISS nude mice. One hundred (100) percent of mice developed subcutaneous (SC) MX-1 tumors.

Treatment was started at day 21 when the tumors reached a mean volume of 146.4+/−139.1 mm³. Ninety (90) mice were randomized into 9 groups of 10 mice each. The mean tumor volume of each group was not statistically different from the other groups (analysis of variance).

Satraplatin was suspended in arachis oil (Sigma, Nr. P-2144) at 0.5, 1.5, 2.5, 3.5 or 4.5 mg/ml by sonication (Transsonic 700/H) on every day of administration. Suspensions were continuously agitated during administration to mice. Capecitabine was prepared as described by Zhou et al (Clinical Cancer Res (2003) 9, 6030-7). Capecitabine was suspended in 40 mM citrate buffer pH 6 (Sigma, Nr. S4641) containing 5% Arabic gum (Sigma, Nr. G9752) at 3.6, 54, 75, 90 or 108 mg/ml on every day of administration.

The treatment schedule was as follows (all dosage indicated are dosages per administration):

Mice from group 1 received one daily PO (oral) administration of satraplatin vehicle (arachis oil, see above) for 5 consecutive days from D21 (day 21) to D25 (referred to as Q1D×5) in combination with one daily PO administration of capecitabine vehicle (Citrate buffer containing Arabic gum, see above) for 8 consecutive days from D21 to D28 (Q1D×8), Mice from group 2 received one daily PO administration of capecitabine at 750 mg/kg (milligram per kilogram of body weight) for 8 consecutive days from D21 to D28 (Q1D×8), Mice from group 3 received one daily PO administration of satraplatin at 5 mg/kg for 5 consecutive days from D21 to D25 (Q1D×5), Mice from group 4 received one daily PO administration of satraplatin at 15 mg/kg for 5 consecutive days from D21 to D25 (Q1 D×5), Mice from group 5 received one daily PO administration of satraplatin at 25 mg/kg for 5 consecutive days from D21 to D25 (Q1D×5), Mice from group 6 received one daily PO administration of satraplatin at 45 mg/kg for 5 consecutive days from D21 to D25 (Q1D×5), Mice from group 7 received one daily PO administration of satraplatin at 5 mg/kg for 5 consecutive days from D21 to 025 (Q1D×5) in combination with one daily PO administration of capecitabine at 750 mg/kg for 8 consecutive days from D21 to D28 (Q1D×8), Mice from group 8 received one daily PO administration of satraplatin at 15 mg/kg for 5 consecutive days from D21 to D25 (Q1D×5) in combination with one daily PO administration of capecitabine at 750 mg/kg for 8 consecutive days from D21 to D28 (Q1Dx8), Mice from group 9 received one daily PO administration of satraplatin at 25 mg/kg for 5 consecutive days from D21 to D25 (Q1Dx5) in combination with one daily PO administration of capecitabine at 750 mg/kg for 8 consecutive days from D21 to D28 (Q1Dx8).

Satraplatin was administered 30 minutes after capecitabine. Satraplatin and capecitabine were administered at a dose volume of 10 ml/kg body weight. The treatment schedule is summarized in Table 9.

A marked inhibition of tumor growth was observed for mice treated with satraplatin at 15 and 25 mg/kg. A moderate inhibition of the tumor growth was observed for mice treated with satraplatin at 5 mg/kg and capecitabine at 750 mg/kg alone. In contrast, a marked enhancement of the antitumor activity was observed for mice treated with satraplatin at 5 mg/kg in combination with capecitabine at 750 mg/kg when compared to mice treated with satraplatin or capecitabine alone at the same respective doses.

T/C % values were calculated with the median tumor volumes for each day of tumor measurement from D21 to D43.

TABLE 9

Treatment schedule of the satraplatin plus capecitabine in vivo combination study

| | | Test substance | | | Reference substance | | |
|---|---|---|---|---|---|---|---|
| Group | No. of mice | Treatment (dose) | Adm route | Treatment schedule (days of treatment) | Combined treatment (dose) | Adm route | Treatment schedule (days of treatment) |
| 1 | 10 | Satraplatin vehicle | PO | Q1Dx5 (D21 to D25) | Capecitabine vehicle | PO | Q1Dx8 (D21 to D28) |
| 2 | 10 | — | — | — | Capecitabine (750 mg/kg/adm) | PO | Q1Dx8 (D21 to D28) |
| 3 | 10 | Satraplatin (5 mg/kg/adm) | PO | Q1Dx5 (D21 to D25) | — | — | — |
| 4 | 10 | Satraplatin (15 mg/kg/adm) | PO | Q1Dx5 (D21 to D25) | — | — | — |
| 5 | 10 | Satraplatin (25 mg/kg/adm) | PO | Q1Dx5 (D21 to D25) | — | — | — |
| 6 | 10 | Satraplatin (45 mg/kg/adm) | PO | Q1Dx5 (D21 to D25) | — | — | — |
| 7 | 10 | Satraplatin (5 mg/kg/adm) | PO | Q1Dx5 (D21 to D25) | Capecitabine (750 mg/kg/adm) | PO | Q1Dx8 (D21 to D28) |
| 8 | 10 | Satraplatin (15 mg/kg/adm) | PO | Q1Dx5 (D21 to D25) | Capecitabine (750 mg/kg/adm) | PO | Q1Dx8 (D21 to D28) |
| 9 | 10 | Satraplatin (25 mg/kg/adm) | PO | Q1Dx5 (D21 to D25) | Capecitabine (750 mg/kg/adm) | PO | Q1Dx8 (D21 to D28) |

— not appicable - test or reference substance administered as a monotherapy

During the course of the experiment, viability and behaviour of mice were recorded every day. Mice body weight and tumor volume was recorded twice a week. Mice were terminated when tumor weight was equivalent to 10% of body weight or when a body weight loss of 20% was observed.

Tumor growth inhibition (T/C %) is defined as the ratio of the median tumor volume of a given treated group (test or reference substance) versus the equivalent median volume from the control group. T/C % is calculated as follows:

$$T/C\% = \frac{\text{Median tumor volume of treated group(mm}^3\text{) at Day } X}{\text{Median tumor volume of control group(mm}^3\text{) at Day } X} \times 100$$

The optimal value is the minimal T/C % ratio that reflects the maximal tumor growth inhibition achieved. According to NCI standards, the criteria for a test substance to be considered effective is a T/C ratio of ≦42% (Bull. Cancer (1991) 78, 587). T/C % values higher than 70% correspond to a marginal antitumor activity, T/C % values ranging from 30 to 70% correspond to a moderate antitumor activity whereas T/C % values under 30% correspond to a marked antitumor activity. Tumor Log cell kill was calculated using the following formula:

$$\text{Log cell kill} = \frac{\text{Time to reach a tumor volume of 700 mm}^3 \text{(treated mice} - \text{control mice)}}{3.32 \times DT \text{ of control mice}},$$

wherein DT is the doubling time of the tumor. For subcutaneous growing tumors a treatment is considered as active when log cell kill is >1 (Cancer Res (1982) 42, 1707).

The T/C % parameters, calculated after D29, were found lower than 42% for mice treated with satraplatin at 15 and 25 mg/kg and for mice treated with satraplatin at 5 and 15 mg/kg in combination with capecitabine at 750 mg/kg. T/C % value was equal to 1% at D43 for mice treated with satraplatin at 5 mg/kg in combination with capecitabine at 750 mg/kg, whereas T/C % values were equal to 43 and 68% for mice treated with satraplatin and capecitabine alone at the same respective doses. For the mice treated with satraplatin at 5 mg/kg in combination with capecitabine at 750 mg/kg, tumors resumed growth for 5 mice out of 7 after D47. One mouse was cured (tumor volume was at 0 mm$^3$ at D75) and tumor were palpable for one mouse (tumor volume was at 13.5 mm$^3$ at D75). For the mice treated with satraplatin at 15 mg/kg in combination with capecitabine at 750 mg/kg tumors resumed growth for 1 mouse out of 6 after D61. Three mice were cured (tumor volume was at 0 mm$^3$ at D75) and tumor were palpable for one mouse (tumor volume was at 4 mm$^3$ at D75). Tumor of one mouse remaining with a stable volume and was at 85 mm$^3$ at D75. See Table 10.

The tumor log cell kill value was equal to 1.7 for mice treated with satraplatin at 5 mg/kg in combination with capecitabine at 750 mg/kg, whereas the tumor log cell kill values were 0.2 and 0.3 for mice treated with capecitabine and satraplatin alone at the same respective doses. The tumor log cell kill value was equal to 6.3 for mice treated with satraplatin at 15 mg/kg in combination with capecitabine at 750 mg/kg, whereas the tumor log cell kill values were 0.2 and 2.2 for mice treated with capecitabine and satraplatin alone at the same respective doses. Because of toxic effects, the log cell kill of mice treated with satraplatin at 45 mg/kg and with satraplatin at 25 mg/kg in combination with capecitabine was not calculated.

TABLE 10

Antitumor activity study of satraplatin and capecitabine administered in combination -
Summary table of median tumor volumes and T/C %.

| Groups | Treatments (dose) | Parameters | D21 | D26 | D29 | D33 | D36 | D40 | D43 |
|---|---|---|---|---|---|---|---|---|---|
| 1 | Satraplatin vehicle and capecitabine vehicle | Median tumor volume (mm$^3$) | 79.7 | 190.4 | 399.7 | 763.3 | 1154.3 | 1580.9 | 2342.6 |
|   |   | T/C % | 100 | 100 | 100 | 100 | 100 | 100 | 100 |
| 2 | Capecitabine (750 mg/kg/adm) | Median tumor volume (mm$^3$) | 98.8 | 217.5 | 322.1 | 498.2 | 711.0 | 1046.3 | 1598.0 |
|   |   | T/C % | 124 | 114 | 81 | 65 | 62 | 66 | 68 |
| 3 | Satraplatin (5 mg/kg/adm) | Median tumor volume (mm$^3$) | 102.5 | 240.4 | 331.2 | 459.9 | 590.5 | 913.0 | 997.2 |
|   |   | T/C % | 129 | 126 | 83 | 60 | 51 | 58 | 43 |
| 4 | Satraplatin (15 mg/kg/adm) | Median tumor volume (mm$^3$) | 103.0 | 201.5 | 123.5 | 35.0 | 16.2 | 11.8 | 13.5 |
|   |   | T/C % | 129 | 106 | 31 | 5 | 1 | 1 | 1 |
| 5 | Satraplatin (25 mg/kg/adm) | Median tumor volume (mm$^3$) | 105.0 | 163.2 | 66.7 | 25.7 | 16.2 | 8.8 | 8.8 |
|   |   | T/C % | 132 | 86 | 17 | 3 | 1 | 1 | 0 |
| 6 | Satraplatin (45 mg/kg/adm) | Median tumor volume (mm$^3$) | 104.7 | 134.1 | 70.1 | 27.0 | 18.2 | 6.8 | 0.0 |
|   |   | T/C % | 131 | 70 | 18 | 4 | 2 | NA | NA |
| 7 | Satraplatin (5 mg/kg/adm) and capecitabine (750 mg/kg/adm) | Median tumor volume (mm$^3$) | 105.5 | 332.3 | 156.6 | 104.2 | 71.6 | 42.4 | 29.1 |
|   |   | T/C % | 132 | 174 | 39 | 14 | 6 | 3 | 1 |
| 8 | Satraplatin (15 mg/kg/adm) and capecitabine (750 mg/kg/adm) | Median tumor volume (mm$^3$) | 101.3 | 225.0 | 186.0 | 98.0 | 63.4 | 20.4 | 9.6 |
|   |   | T/C % | 127 | 118 | 47 | 13 | 5 | 1 | 0 |
| 9 | Satraplatin (25 mg/kg/adm) and capecitabine (750 mg/kg/adm) | Median tumor volume (mm$^3$) | 80.1 | 155.2 | 80.9 | NA | NA | NA | NA |
|   |   | T/C % | 100 | 81 | 20 | NA | NA | NA | NA |

T/C %: Ratio of the median tumor volumes of treated group (T) versus vehicle treated group (C)
NA: Not Applicable (more than 60% of mice died)

Legend:

Median tumor volumes and T/C % were calculated by comparing the median volumes of treated mice with the median volume of none treated mice from D21 to D43. Mice were treated with satraplatin for 5 consecutive days (Q1D×5) or with capecitabine for 8 consecutive days (Q1D×8). Treatments were initiated at D21.

In summary, a significant enhancement of the antitumor activity was observed for mice treated in combination with satraplatin and capecitabine, confirming the synergistic effects observed in the in vitro experiments (Examples 2 and 3).

Example 4.2

Synergism Between the Subject Platinum-based Compounds and Gemcitabine in a Xenograft Model Athymic nude NCr nu/nu mice were used for this study. Animals were purchased from an NCI-approved facility and were acclimated in the laboratories one week prior to experimentation. Animals were observed daily. Tumors were measured twice weekly and the animal body weight was recorded twice weekly as well.

A PANC-1 human pancreatic tumor model was used. PANC-1 (ATCC order number: CRL-1469) is a human tumor cell line isolated from a human carcinoma of the exocrine pancreas (Int J Cancer (1975) 15, 741-7). Thirty to forty mg tumor fragments were implanted subcutaneously into athymic nude nu/nu mice using 12-gauge trocar needles. Mice were implanted with tumor fragments in a weight range as narrow as possible (63-200 mg tumors with a mean of 120 to 160 mg if possible). Animals were randomly placed into the various experimental groups.

TABLE 11

Treatment schedule of the satraplatin plus gemcitabine in vivo combination study

| Group No. | Compound | Dosage (mg/kg/injection) | Treatment Schedule and Route |
|---|---|---|---|
| 1 | Vehicle | 0 | q1d x 5, po |
| 2 | Satraplatin | 35 | q1d x 5, po |
| 3 |  | 20 |  |
| 4 | Gemcitabine | 120 | q3d x 4, ip |
| 5 |  | 100 |  |
| 6 | Satraplatin | 20 | q1d x 5, po |
|   | Gemcitabine | 120 | q3d x 4, ip |
| 7 | Satraplatin | 35 | q1d x 5, po |
|   | Gemcitabine | 100 | q3d x 4, ip |
| 8 | Satraplatin | 20 | q1d x 5, po |
|   | Gamcitabine | 100 | q3d x 4, ip |

For other experimental details see Example 4.1.

Results are shown in FIG. 3. Tumor volumes of mice treated with satraplatin and gemcitabine in combination are clearly smaller than tumor volumes of mice treated with each of the compounds, satraplatin or gemcitabine, individually.

This significant enhancement of the antitumor activity in mice treated with a combination of satraplatin and gemcitabine further confirms the synergistic effects observed in the in vitro experiments (Examples 2 and 3).

Example 4.3

Synergism Between the Subject Platinum-based Compounds and an Inhibitor of a Receptor of the EGFR Family or a Chemotherapeutically Active Pyrimidine Analogue in a Xenograft Model The surprising finding of synergy between the subject platinum-based compounds and an inhibitor of a receptor of the EGFR family or a chemotherapeutically active pyrimidine analogue is confirmed and validated in mouse xenograft models.

Athymic female nu/nu mice (6-8 weeks old; obtained from Charles River Inc., Wilmington/Mass., USA) are allowed to acclimate for at least five days. The human non small cell lung cancer (NSCLC) cell line H460 is used (ATCC deposit number HTB-177). H460 cells are cultured in modified RPMI-1640 complete medium supplied with 10% fetal calf serum (FCS) and 1% Penicillin/Streptomycin.

On Day 0 mice are inoculated with 0.1 ml ($2.5 \times 10^6$ cells) of a cell suspension of H460 cells ($2.5 \times 10^7$ cells/ml in incomplete medium) by subcutaneous injection into the area of the mammary fat pad under light anesthesia. The take rate is 100%. When the average tumor weight reaches about 100 mg (Day 7), animals with an average tumor size of 130 mg are selected and randomly divided into the appropriate animal groups.

An inhibitor of a receptor of the EGFR family or a chemotherapeutically active pyrimidine analogue is dissolved in the appropriate medium and additives are added, if required. The stock solution is freshly diluted 1:10 with 5% glucose immediately prior to use. The inhibitor of a receptor of the EGFR family or the chemotherapeutically active pyrimidine analogue is administered intravenously (iv), for example every 7 days for two times, starting on day 7, i.e. on days 7 and 14. Control groups receive ETG (50% ethanol/50% Tween-80 diluted 1:10 with 5% glucose) intravenously.

Satraplatin (JM-216) or JM-118 is formulated in peanut oil on each dosing day. Satraplatin or JM-118 is weighed in individual tubes for different dosing groups and suspended in appropriate amounts of peanut oil. The suspensions are sonicated for 10 minutes, then vortexed for 10 seconds and are administered within 30 minutes after preparation. Control groups receive peanut oil. Satraplatin or JM-118 is administered orally (po), using a 20G gavage needle, for example starting on day 8 for five consecutive days, followed by a two days interval and then five additional consecutive days of treatment (i.e. treatment on days 8-12 and 15-19).

The volume of administration for both, iv and po treatments, is 0.1 ml per 10 grams of body weight. Tumor growth and body weight are monitored and recorded three times a week.

The combination treatment, in which an inhibitor of a receptor of the EGFR family or a chemotherapeutically active pyrimidine analogue and satraplatin are administered sequentially, is clearly more effective than the individual administration of an inhibitor of a receptor of the EGFR family or a chemotherapeutically active pyrimidine analogue or satraplatin. These experiments confirm the synergistic effect of the in vitro studies.

What is claimed is:

1. A method for the treatment of an individual suffering from a cancer or a tumor, comprising administering to said individual in need thereof, a first pharmaceutical composition comprising a platinum-based chemotherapeutic agent, wherein said agent is, or on said administration results in, a compound of formula II:

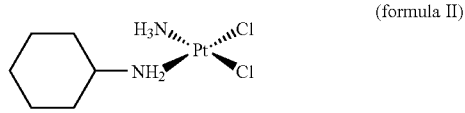

and administering to said individual, a second pharmaceutical composition comprising an inhibitor of a receptor of the EGFR family or a chemotherapeutically active pyrimidine analogue and wherein said first pharmaceutical composition and said second pharmaceutical composition are administered to said individual within 14 days of each other.

2. A method of using a first pharmaceutical composition containing an inhibitor of a receptor of the EGFR family or a chemotherapeutically active pyrimidine analogue for the treatment of an individual suffering from a cancer or a tumor, comprising administering said inhibitor or analogue to said individual within about 14 days of administration of a second pharmaceutical composition containing a platinum-based chemotherapeutic agent and wherein said platinum-based chemotherapeutic agent is, or on administration results in, a compound of formula II:

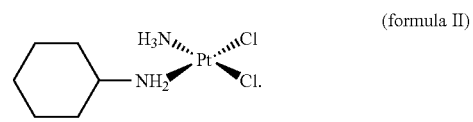

3. A method of using a platinum-based chemotherapeutic agent for the preparation of a first pharmaceutical composition for the treatment of an individual suffering from a cancer or a tumor, wherein said treatment is a combination treatment comprising administering said first pharmaceutical composition and administering a second pharmaceutical composition comprising an inhibitor of a receptor of the EGFR family or a chemotherapeutically active pyrimidine analogue, wherein said first and second pharmaceutical compositions are administered within 14 days of each other and wherein said platinum-based chemotherapeutic agent is, or on administration results in, a compound of formula II:

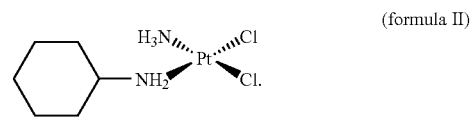

4. A method of using an inhibitor of a receptor of the EGFR family or a chemotherapeutically active pyrimidine analogue for the preparation of a first pharmaceutical composition for the treatment of an individual suffering from a cancer or a tumor, wherein said treatment is a combination treatment comprising administering said first pharmaceutical composition and administering a second pharmaceutical composition comprising a platinum-based chemotherapeutic agent, wherein said first and second pharmaceutical compositions are administered within 14 days of each other and wherein said platinum-based chemotherapeutic agent is, or on administration results in, a compound of formula II:

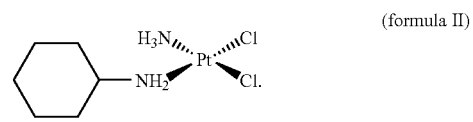

5. The method according to any one of claims 1, 2, 3 or 4, wherein said administration:
(i) is the sequential administration to said individual of an inhibitor of a receptor of the EGFR family or a chemotherapeutically active pyrimidine analogue and a platinum-based chemotherapeutic agent within from 1 day to 10 days of each other; or (ii) results in the sequential contact of a cell included in, derived from or being part of said cancer or tumour with an inhibitor of a receptor of the EGFR family or a chemotherapeutically active pyrimidine analogue and a platinum-based chemotherapeutic agent within from 1 day to 10 days of each other.

6. The method according to any one of claims 1, 2, 3 or 4 wherein said administration:
   (i) is the sequential administration to said individual of an inhibitor of a receptor of the EGFR family or a chemotherapeutically active pyrimidine analogue and a platinum-based chemotherapeutic agent within 5 minutes to 48 hours of each other; or
   (ii) results in the sequential contact of a cell included in, derived from or being part of said cancer or tumour with an inhibitor of a receptor of the EGFR family or a chemotherapeutically active pyrimidine analogue and a platinum-based chemotherapeutic agent within 5 minutes to 48 hours of each other.

7. The method according to any one of claims 1, 2, 3 or 4, wherein the first and second pharmaceutical compositions are administered to said individual effectively at the same time.

8. The method of claim 1, wherein said cancer or said tumor is included in a solid tumor, is derived from a solid tumor, or is a solid tumor.

9. The method of claim 8, wherein said solid tumor is selected from the group consisting of: prostate cancer, breast cancer, cervical cancer, colorectal cancer, peritoneal cancer, ovarian cancer, bronchial cancer, small cell lung cancer, non-small cell lung cancer, gastric, and head and neck cancer, or metastases thereof.

10. The method of claim 1, wherein said cancer or said tumor is included in a hematological tumor, is derived from a hematological tumor, or is a hematological tumor.

11. The method of claim 9, wherein said solid tumor is prostate cancer and wherein said prostate cancer is hormone-refractory prostate cancer.

12. The method of claim 1, wherein said cancer or said tumor is a tumor or a cancer resistant or refractory to an anti-proliferative agent.

13. The method of claim 12, wherein said anti-proliferative agent is cisplatin.

14. The method of claim 12, wherein said anti-proliferative agent is not a hormone-based drug.

15. The method of any one of claims 1, 2, 3 or 4, wherein the pharmaceutical composition containing a platinum-based chemotherapeutic agent is administered orally.

16. The method of any one of claims 1, 2, 3 or 4, wherein the pharmaceutical composition containing an inhibitor of a receptor of the EGFR family or a chemotherapeutically active pyrimidine analogue is administered intravenously.

17. The method of any one of claims 1, 2, 3 or 4, wherein the platinum-based chemotherapeutic agent is administered at a dose of from 1 microgram per kilogram of weight of the individual being treated to about 500 milligrams per kilogram of weight of the individual being treated.

18. The method of any one of claims 1, 2, 3 or 4, wherein the platinum-based chemotherapeutic agent is administered at a dose of from 50 micrograms per square meter of the individual's body surface area to 15 grams per square meter of the individual's body surface area.

19. The method of any one of claims 1, 2, 3 or 4, wherein the inhibitor of a receptor of the EGFR family or the chemotherapeutically active pyrimidine analogue is administered at a dose of from 1 microgram per kilogram of weight of the individual being treated to 500 milligrams per kilogram of the weight of the individual being treated.

20. The method of any one of claim 1, 2, 3 or 4, wherein the inhibitor of a receptor of the EGFR family or the chemotherapeutically active pyrimidine analogue is administered at a dose of from 50 micrograms per square meter of body surface area to 15 grams per square meter of body surface area.

* * * * *